United States Patent
Sarwal et al.

(10) Patent No.: US 9,535,075 B2
(45) Date of Patent: Jan. 3, 2017

(54) PROTEIN AND GENE BIOMARKERS FOR REJECTION OF ORGAN TRANSPLANTS

(75) Inventors: Minnie M. Sarwal, Portola Valley, CA (US); Tara Sigdel, Palo Alto, CA (US); Amit Kaushal, Los Altos, CA (US); Li Li, Fremont, CA (US); Wenzhong Xiao, San Jose, CA (US); Atul J. Butte, Menlo Park, CA (US); Purvesh Khatri, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 13/635,667

(22) PCT Filed: Mar. 25, 2011

(86) PCT No.: PCT/US2011/030026
§ 371 (c)(1),
(2), (4) Date: Feb. 21, 2013

(87) PCT Pub. No.: WO2011/119980
PCT Pub. Date: Sep. 29, 2011

(65) Prior Publication Data
US 2013/0143755 A1 Jun. 6, 2013

Related U.S. Application Data

(60) Provisional application No. 61/341,071, filed on Mar. 25, 2010, provisional application No. 61/452,288, filed on Mar. 14, 2011.

(51) Int. Cl.
C12Q 1/68 (2006.01)
G01N 33/68 (2006.01)

(52) U.S. Cl.
CPC ......... *G01N 33/6893* (2013.01); *C12Q 1/6809* (2013.01); *C12Q 1/6883* (2013.01); *C12Q 2600/158* (2013.01); *G01N 2800/245* (2013.01)

(58) Field of Classification Search
None
See application file for complete search history.

(56) References Cited

U.S. PATENT DOCUMENTS

| | | |
|---|---|---|
| 6,235,311 B1 | 5/2001 | Ullah |
| 6,607,879 B1 | 8/2003 | Cocks et al. |
| 7,026,121 B1 | 4/2006 | Wohlgemuth et al. |
| 7,879,556 B2 | 2/2011 | Wohlgemuth et al. |
| 2003/0017619 A1 | 1/2003 | Rokubo et al. |
| 2003/0104371 A1 | 6/2003 | Strom et al. |
| 2004/0163654 A1 | 8/2004 | Williams et al. |
| 2005/0025769 A1* | 2/2005 | Kobayashi .......... A61K 38/13 424/145.1 |
| 2006/0088836 A1 | 4/2006 | Wohlgemuth et al. |
| 2006/0088876 A1 | 4/2006 | Bauer et al. |
| 2006/0246485 A1 | 11/2006 | Sarwal et al. |
| 2006/0269949 A1 | 11/2006 | Halloran et al. |
| 2006/0281122 A1 | 12/2006 | Bryant et al. |
| 2007/0031890 A1 | 2/2007 | Wohlgemuth et al. |
| 2007/0111210 A1 | 5/2007 | Bigaud et al. |
| 2007/0122806 A1 | 5/2007 | Strom et al. |
| 2007/0134728 A1 | 6/2007 | Hu et al. |
| 2007/0212701 A1 | 9/2007 | O'Toole et al. |
| 2007/0232658 A1 | 10/2007 | Wagner et al. |
| 2007/0264272 A1 | 11/2007 | Perreault et al. |
| 2008/0233573 A1 | 9/2008 | Storm et al. |
| 2009/0022730 A1 | 1/2009 | Raulf et al. |
| 2009/0197286 A1 | 8/2009 | Karin et al. |
| 2009/0269334 A1 | 10/2009 | Bigaud et al. |
| 2009/0304705 A1 | 12/2009 | Grass et al. |

(Continued)

FOREIGN PATENT DOCUMENTS

| | | |
|---|---|---|
| EP | 1731620 | 12/2006 |
| EP | 2295966 | 3/2011 |

(Continued)

OTHER PUBLICATIONS

Anglicheau et al. (Noninvasive prediction of organ graft rejection and outcome using gene expression patterns, Transplantation. Jul. 27, 2008;86(2):192-9).*
Li; et al., "A Peripheral Blood Diagnostic Test for Acute Rejection in Renal Transplantation", American Journal of Transplantation (Oct. 2012), 12(10):2710-2718.
"Affymetrix Human Genome U133 Plus 2.0 Array", Gene Expression Omnibus (Nov. 2003), XP002627319, 3 pgs.

(Continued)

*Primary Examiner* — Aaron Priest
(74) *Attorney, Agent, or Firm* — Bret E. Field; Bozicevic, Field & Francis LLP

(57) ABSTRACT

Aspects of the present invention include methods for determining a transplant category of a subject having a transplant. Common mechanisms of rejection injury are uncovered across different tissue transplants, and provide a means to understand rational drug design. Various sources of tissues are examined form the patient for understanding AR mechanism (graft biopsy), as well as monitoring by minimal invasive means (blood) or non-invasive means (urine for the kidney allograft). For biomarker discovery different categories of markers are examined such as genes, proteins, peptides and antibodies. These biomarkers can help determine the subject's transplant category (e.g., acute allograft rejection (AR), stable allograft (STA), BK viremia, BK nephritis, drug toxicity or chronic allograft injury (CAI), and the like). Also provided are compositions, systems, kits and computer program products that find use in practicing the subject methods. The methods and compositions find use in a variety of applications.

23 Claims, 9 Drawing Sheets

(56) References Cited

U.S. PATENT DOCUMENTS

| | | |
|---|---|---|
| 2010/0120629 A1 | 5/2010 | Ellis et al. |
| 2010/0298245 A1 | 11/2010 | Aydt et al. |
| 2011/0171645 A1 | 7/2011 | McManus et al. |
| 2011/0201519 A1 | 8/2011 | Sarwal et al. |
| 2013/0157888 A1 | 6/2013 | Nagele |

FOREIGN PATENT DOCUMENTS

| | | |
|---|---|---|
| WO | 2004/074815 | 9/2004 |
| WO | 2005/005601 | 1/2005 |
| WO | 2005/070086 | 8/2005 |
| WO | 2007/104537 | 9/2007 |
| WO | 2007/121922 | 11/2007 |
| WO | 2008/009132 | 1/2008 |
| WO | 2008/084331 | 7/2008 |
| WO | 2009/143624 | 12/2009 |
| WO | 2010038974 | 8/2010 |

OTHER PUBLICATIONS

Al-Lamki; et al., "Expression of Tumor Necrosis Factor Receptors in Normal Kidney and Rejecting Renal Transplants", Laboratory Investigation (Nov. 2001), 81(11):1503-1515.

Chen; et al., "Differentially Expressed RNA from Public Microarray Data Identifies Serum Protein Biomarkers for Cross-Organ Transplant Rejection and Other Conditions", PLOS Computational Biology (Sep. 2010), 6(9):e1000940.

Hardiman, "Microarray platforms—comparisons and contrasts", Pharmacogenomics (Jan. 2004), 5(5): 487-502.

Hauser; et al., "Prediction of Acute Renal Allograft Rejection by Urinary Monokine Induced by IFN-gamma (MIG)", The American Society of Nephrology (Jan. 2005), 16(6):1849-1858.

Hidalgo; et al., "The Transcriptome of Human Cytotoxic T Cells: Measuring the Burden of CTL-Associated Transcripts in Human Kidney Transplants", American Journal of Transplantation (Mar. 2008), 8(3):637-646.

Mengel; et al., "Scoring Total Inflammation Is Superior to the Current Banff Inflammation Score in Predicting Outcome and the Degree of Molecular Disturbance in Renal Allografts", American Journal of Transplantation (Aug. 2009), 9(8):1859-1867.

Morgun; et al., "Molecular Profiling Improves Diagnoses of Rejected and Infection in Transplanted Organs", Circulation Research (Jun. 2006), 98(12):e74-83.

"GeneChip 3' IVT Plus Reagent Kit", Affymetrix (2013), User Manual, 45 pgs.

Butte; et al., "Protein microarrays discover angiotensinogen and PRKRIP1 as novel targets for autoantibodies in chronic renal disease", Mol Cell Proteomics (Mar. 2011), 10(3):M110.000497.

Cox; et al., "Altered modulation of WNT-beta-catenin and PI3K/Akt pathways in IgA nephropathy", Kidney Int (Aug. 2010), 78(4):396-407.

Dinarello; et al., "Anti-inflammatory Agents: Present and Future", Cell (Mar. 2010), 140(6):935-950.

Ismail; et al., "Important fluorinated drugs in experimental and clinical use", Journal of Fluorine Chemistry (Dec. 2002), 118(1):27-33.

Kalil; et al., "Meta-analysis: the efficacy of strategies to prevent organ disease by cytomegalovirus in solid organ transplant recipients", Ann Intern Med (Dec. 2005), 143(12):870-880.

Kaposztas; et al., "Impact of rituximab therapy for treatment of acute humoral rejection", Clin Transplant (Jan.-Feb. 2009), 23(1):63-73.

Metz; et al., "Application of proteomics in the discovery of candidate protein biomarkers in a diabetes autoantibody standardization program sample subset", J Proteome Res (Feb. 2008), 7(2):698-707.

Sato; et al., "Aberrant CD3- and CD3-mediated signaling events in cord blood T Cells are associated with dysfunctional regulation of Fas ligand-mediated cytotoxicity", The Journal of Immunology (Apr. 1999), 162(8):4464-4471.

Sigdel; et al., "Profiling of autoantibodies in IgA nephropathy, an integrative antibiomics approach", Clin J Am Soc Nephrol (Dec. 2011), 6(12):2775-2784.

Agilent-014850 whole human genome microarray 4x44K G4112F (Probe Name Version), GEO (2008), XP002594592.

Akalin; et al. "Gene expression analysis in human renal allograft biopsy samples using high-density oligoarray technology", Transplantation (2001), 72(5):948-53.

Alarcon; et al. "Time to renal disease and end-stage renal disease in Profile: a multiethnic lupus cohort", PLos Med (Oct. 2006), 3(10):e396.

Brouard; et al. "Identification of a peripheral blood transcriptional biomarker panel associated with operational renal allograft tolerance", PNAS (2007), 104(39):15448-15453.

Carvalho-Gaspar; et al. "Chemokine gene expression during allograft rejection: Comparison of two quantitative PCR techniques", Journal of Immunological Methods (2005), 301(1-2):41-52.

Chan; et al. "Integrating Transcriptomics and Proteomics", Drug Discovery and Development (2006), printed from www.ddmag.com, 6 pages.

Chen; et al. "Discordant protein and mRNA expression in lung adenocarcinomas", Molecular and Cellular Proteomics (2002), 1(4):304-13.

Cheung; et al. "Natural Variation in Human Gene Expression Assessed in Lymphoblastoid Cells," Nature Genetics (2003), 33:422-425.

Chu; et al. "Cloning of a new "finger" protein gene (ZNF173) within the class I region of the human MHC", Genomics (1995), 29(1):229-39.

Chua; et al. "Applications of Microarrays to Renal Transplantation: Progress and Possibilities" Frontiers in Bioscience (2003), 8:S913-23.

Database Embl [Online], "Thymidine Kinase, Cytosolic (human), mRNA Sequence", (1998), 2pages, XP002434108, Database accession No. AA778098.

Dugré; et al. "Cytokine and cytotoxic molecule gene expression determined in peripheral blood mononuclear cells in the diagnosis of acute renal rejection.", Transplantation (2000), 70(7):1074-1080.

Enard; et al. "Intra- and interspecific variation in primate gene expression patterns", Science (Apr. 2002), 296 (5566):340-343.

Farivar; et al. "The role of CC and CXC chemokines in cardiac allograft rejection in rats", Experimental and Molecular Pathology (2005), 78(3):171-176.

Flechner; et al. "Kidney transplant rejection and tissue injury by gene profiling of biopsies and peripheral blood lymphocytes", American Journal of Transplantation (2004), 4(9):1475-89.

Fujiwaki; et al. "Thymidine Kinase in Epithelial Ovarian Cancer: Relationship with the Other Pyrimidine Pathway Enzymes", Int. J. Cancer (2002), 99(3):328-335.

Gimino; et al. "Gene Expression Profiling of Broncholveolar Lavage Cells in Acute Lung Rejection," American Journal of Respiratory and Critical Care Medicine (2003), 168:1237-1242.

Gronowitz; et al. "Serum Thymidine Kinase in Transplant Patients: Its Relation to Cytomegalovirus Activity, Renal Transplant Rejection and its Use for Monitoring of Antiviral Therapy", Annals of Clinical Research (1986), 18(2):71-75.

Gwinner; et al. "Renal transplant rejection markers." World J Urol (Oct. 2007), 25(5):445-455.

Hernandez-Fuentes; et al. "Immunologic monitoring", Immunological Reviews (2003), 196:247-264.

Horwitz; et al. "Detection of Cardiac Allograft Rejection and Response to Immunosuppressive Therapy with Peripheral Blood Gene Expression," Circulation (2004), 110:3815-3821.

Jevnikar; et al. "Late Kidney Allograft Loss: What We Know About It, and What We Can Do About It", Clin J Am Soc Nephrol (2008), 3(S56-S67).

Joosten; et al. "Chronic Renal Allograft Rejection: Pathophysiologic Considerations", Kidney International (2005), 68:1-13.

Lang; et al. "DUSP meet immunology: dual specificity MAPK phosphatases in control of the inflammatory response", J Immunol (Dec. 2006), 177(11):7497-504.

(56) References Cited

OTHER PUBLICATIONS

Lee; et al. "Expression profiling of murine double-negative regularoty T cells suggest mechanisms for prolonged cardiac allograft survival", J. Immunol. (2005), 174(8):4535-4544.
Li; et al. "Identifying compartment-specific non-HLA targets after renal transplantation by integrating transcriptome and "antibodyome" measures", PNAS (2009), 106(11):4148-4153.
Ling; et al. "Integrative urinary peptidomics in renal transplantation identifies biomarkers for acute rejection", J Am Soc Nephrol (Apr. 2010), 21(4):646-653.
Mansfield; et al. "Arraying the Orchestration of Allograft Pathology", American Journal of Transplantation (2004), 4(6):853-862.
Marsden; et al. "Predicting Outcomes after Renal Transplantation—New Tools and Old Tools," The New England Journal of Medicine (2003), 349(2):182-184.
Martinez-Llordella; et al. "Using transcriptional profiling to develop a diagnostic test of operational tolerance in liver transplant recipients", The Journal of Clinical Investigations (2008), 118(8):2845-2857.
McMorrow; et al. "New intra-renal graft genes associated with tolerance or rejection", Kidney International, symp. 1 (2002), 61: S85-S93.
Medbury; et al. "The Cytokine and Histological Response in Islet Xenograft Rejection is Dependent Upon Species Combination," Transplantation (1997), 64(9):1307-1314.
Midha; et al. "Chemokine Expression in Nerve Allografts," Neurosurgery (2004), 54(6):1472-149.
O'Riordan; et al. "Bioinformatic Analysis of the Urine Proteome of Acute Allograft Rejection," Journal of American Society of Nephrology (2004), 15:3240-3248.
Rotondi; et al. "High pretransplant serum levels of CXCL9 are associated with increased risk of acute rejection and graft failure in kidney graft recipients", Transpl Int (May 2010), 23(5):465-475.
Sarwal; et al. "Integrative Genomics to Identify Non-HLA Allogenic Kidney-Specific Targets after Kidney Transplantation", Transplantation (2008), 86(2S):13, Oral Abstracts, downloaded Apr. 6, 2010.
Sarwal; et al. "Molecular Heterogeneity in Acute Renal Allograft Rejection Identified by DNA Microarray Profiling," New England Journal of Medicine (2003), 349:125-138.
Scherer; et al. "Early Prognosis of the Development of Renal Chronic Allograft Rejection by Gene Expression Profiling of Human Protocol Biopsies", Transplantation (2003), 75(8):1323-30.
Serody; et al. "T-lymphocyte production of macrophage inflammatory protein-lalpha is critical to the recruitment of CD8(+) T cells to the liver, lung, and spleen during graft-versus-host disease", Blood (2000), 96(9):2973-2980.
Shi; et al. "[Clinical significance of RANTES and MIP-1 alpha in acute rejection episode in kidney transplantation]", Zhongguo Yi Xue Ke Xue Yuan Xue Bao (2004), abstract.
Sigdel; et al. "Shotgun proteomics identifies proteins specific for acute renal transplant rejection", Proteomics Clin Appl (Jan. 2010), 4(1):32-47.
Simon; et al., "Serial Peripheral Blood Perforin and Granzyme B Gene Expression Measurements for Prediction of Acute Rejection in Kidney Graft Recipients," American Journal of Transplantation (2003), 3:1121-1127.
Teramoto; et al. "DNA Synthesis in Hepatocytes During Liver Allograft Rejection in Rats", Transplantation (1990), 50(2):199-201.
Thomson; et al. "Monitoring the Patient Off Immunosuppression" Transplantation (2001), 72(8):S13-S22.
Voshol; et al. "Evaluation of biomarker discovery approaches to detect protein biomarkers of acute renal allograft rejection", J Proteome Res (Jul.-Aug. 2005), 4(4):1192-1199.
Wakui; et al. "Genes Highly Expressed in the Early Phase of Murine Graft-Versus-Host Reaction," Biochemical and Biophysical Communications (2001), 282:200-206.
Whitfield; et al., "Systemic and Cell Type-Specific Gene Expression Patterns in Scleroderma Skin," Proc. Natl. Acad Sci. (2003), 100(21):12319-12324.
Wu; et al. "Analysing Gene Expression Data From DNA Microarrays to Identify Candidate Genes," Journal of Pathology (2001), 195:53-65.
Zhang; et al. "Microarray Analysis of Gene Expression in Peripheral Blood Mononuclear Cells Derived From Long-Surviving Renal Recipients", Transplantation Proceedings (2002), 34:1757-1759.
Roedder; et al., "The pits and pearls in translating operational tolerance biomarkers into clinical practice", Current Opinion in Organ Transplantation (Dec. 2012), 17(6):655-662.
Gerrits; et al., "Donor-reactive cytokine production after HLA-identical living related kidney transplantation: a protein-array analysis", (Nov. 2006), 38(9):2825-7.
Joosten; et al., "Antibody response against the glomerular basement membrane protein agrin in patients with transplant glomerulopathy", American Journal of Transplantation (Feb. 2005), 5(2):383-93.
Mizutani; et al., "Frequency of MIC antibody in rejected renal transplant patients without HLA antibody", Human Immunology (Mar. 2006), 67(3):223-9.
Akalin; et al., "Bocking Cell Microtubule Assembly Inhibits the Alloimmune Response In Vitro and Prolongs Renal Allograft Survival by Inhibition of Th1 and Sparing of Th2 Cell Function In Vivo", Journal of the American Society of Nephrology (1995), 5(7):1418-1425.
Braud; et al., "Immunosuppresive Drug-Free Operational Immune Tolerance in Human Kidney Transplant Recipients: Part 1. Blood Gene Expression Statistical Analysis", Journal of Cellular Biochemistry (Apr. 2008),103(6):1681-1692.
Hauge; et al., "Characterization of the FAM110 gene family", Genomics (May 2007), 90:14-27.
Hillier; et al., "Generation and annotation of the DNA sequences of human chromosomes 2 and 4", Nature (2005), 434:724-731.
Matsuki; et al., "Novel regulation of MHC class II function in B cells", The EMBO Journal (Jan. 2007), 26:846-854.
Saint-Mezard; et al., "Analysis of independent microarray datasets of renal biopsies identifies a robust transcript signature of acute allograft rejection", Transplant International (Mar. 2009), 22(3):293-302.
Famulski; et al., "Changes in the Transcriptome in Allograft Rejection: IFN-.gamma.-Induced Transcripts in Mouse Kidney Allografts", American Journal of Transplantation (Jun. 2006), 6(6):1342-1354.
Nesslinger; et al., "A viral vaccine encoding prostate-specific antigen induces antigen spreading to a common set of self-proteins in prostate cancer patients", Clinical Cancer Research (Aug. 2010), 16(15):4046-4056.
Communal; et al. "Reciprocal modulation of mitogen-activated protein kinases and mitogen-activated protein kinase phosphatase 1 and 2 in failing human myocardium", J Cardiac Failure (Apr. 2002), 8(2):86-92.
Shiro, "Organ Transplant and Molecular Pathology", Journal of the Japan Society for Transplantation, (2004), 39, [2], p. 138-144.
Asberg et al. ("Bilateral Pharmacokinetic Interaction Between Cyclosporine A and Atorvastatin in Renal Transplant Recipients", American Journal of Transplantation, 2001, pp. 382-386.
Kazutoshi Takahashi et al: "Induction of Pluripotent Stem Cells from Adult Human Fibroblasts by Defined Factors", Cell, Cell Press, US, vol. 131, No. 5, Nov. 30, 2007 (Nov. 30, 2007), pp. 861-872.
Schade et al., "Dasatinib, a small-molecule protein tyrosine kinase inhibitor, inhibits T-cell activation and proliferation", Immunobiology, Epub 2007, pp. 1366-1377.

\* cited by examiner

| Tissue | Number of Tissue Specific genes | P-value (Hypergeometric) | FDR (Benjamini-Hochberg) |
|---|---|---|---|
| WHOLEBLOOD | 66 | 8.18E-35 | 1.49E-33 |
| CD4+T-cells | 60 | 8.93E-22 | 1.30E-20 |
| CD8+T-cells | 61 | 1.48E-20 | 1.80E-19 |
| PB-CD14+Monocytes | 58 | 7.48E-20 | 7.80E-19 |
| PB-CD56+NKCells | 65 | 2.02E-19 | 1.85E-18 |
| bonemarrow | 27 | 3.96E-18 | 2.89E-17 |
| PB-BDCA4+Dentritic_Cells | 64 | 2.22E-17 | 1.47E-16 |
| BM-CD33+Myeloid | 59 | 3.18E-17 | 1.94E-16 |
| PB-CD19+Bcells | 49 | 6.89E-13 | 3.59E-12 |
| 721_B_lymphoblasts | 54 | 4.24E-08 | 1.72E-07 |
| BM-CD34+ | 46 | 1.09E-07 | 4.20E-07 |
| BM-CD105+Endothelial | 27 | 6.04E-03 | 1.70E-02 |

FIG. 1D

SEQUENCE LISTING

```
<160> NUMBER OF SEQ ID NOS: 12

<210> SEQ ID NO 1
<211> LENGTH: 13
<212> TYPE: PRT
<213> ORGANISM: human

<400> SEQUENCE: 1

Gly Pro Pro Gly Pro Pro Gly Pro Pro Gly Pro Pro Ser
1               5                   10

<210> SEQ ID NO 2
<211> LENGTH: 13
<212> TYPE: PRT
<213> ORGANISM: human

<400> SEQUENCE: 2

Gly Glu Pro Gly Pro Pro Gly Pro Pro Gly Asn Leu Gly
1               5                   10

<210> SEQ ID NO 3
<211> LENGTH: 13
<212> TYPE: PRT
<213> ORGANISM: human
```

-continued

```
<400> SEQUENCE: 3

Gly Leu Pro Gly Pro Pro Gly Pro Lys Gly Pro Arg Gly
1               5                  10

<210> SEQ ID NO 4
<211> LENGTH: 13
<212> TYPE: PRT
<213> ORGANISM: human

<400> SEQUENCE: 4

Ala Pro Gly Asp Arg Gly Glu Pro Gly Pro Pro Gly Pro
1               5                  10

<210> SEQ ID NO 5
<211> LENGTH: 16
<212> TYPE: PRT
<213> ORGANISM: human

<400> SEQUENCE: 5

Gly Pro Pro Gly Pro Pro Gly Pro Pro Gly Pro Pro Gly Pro Pro Ser
1               5                  10                  15

<210> SEQ ID NO 6
<211> LENGTH: 18
<212> TYPE: PRT
<213> ORGANISM: human

<400> SEQUENCE: 6

Pro Gly Leu Pro Gly Gln Val Gly Glu Thr Gly Lys Pro Gly Ala Pro
1               5                  10                  15

Gly Arg

<210> SEQ ID NO 7
<211> LENGTH: 18
<212> TYPE: PRT
<213> ORGANISM: human

<400> SEQUENCE: 7

Gly Ile Lys Gly Glu Lys Gly Asn Pro Gly Gln Pro Gly Leu Pro Gly
1               5                  10                  15

Leu Pro

<210> SEQ ID NO 8
<211> LENGTH: 21
<212> TYPE: PRT
<213> ORGANISM: human

<400> SEQUENCE: 8

Asn Gly Asp Asp Gly Glu Ala Gly Lys Pro Gly Arg Pro Gly Glu Arg
1               5                  10                  15

Gly Pro Pro Gly Pro
                20

<210> SEQ ID NO 9
<211> LENGTH: 20
<212> TYPE: PRT
<213> ORGANISM: human

<400> SEQUENCE: 9

Asp Gly Pro Pro Gly Arg Asp Gly Gln Pro Gly His Lys Gly Glu Arg
1               5                  10                  15
```

```
<210> SEQ ID NO 10
<211> LENGTH: 32
<212> TYPE: PRT
<213> ORGANISM: human

<400> SEQUENCE: 10

Glu Ser Gly Arg Glu Gly Ala Pro Gly Ala Glu Gly Ser Pro Gly Arg
 1               5                  10                  15

Asp Gly Ser Pro Gly Ala Lys Gly Asp Arg Gly Glu Thr Gly Pro Ala
            20                  25                  30

<210> SEQ ID NO 11
<211> LENGTH: 15
<212> TYPE: PRT
<213> ORGANISM: human

<400> SEQUENCE: 11

Val Ile Asp Gln Ser Arg Val Leu Asn Leu Gly Pro Ile Thr Arg
 1               5                  10                  15

<210> SEQ ID NO 12
<211> LENGTH: 18
<212> TYPE: PRT
<213> ORGANISM: human

<400> SEQUENCE: 12

Ser Gly Ser Val Ile Asp Gln Ser Arg Val Leu Asn Leu Gly Pro Ile
 1               5                  10                  15

Thr Arg
```

PROTEIN AND GENE BIOMARKERS FOR REJECTION OF ORGAN TRANSPLANTS

BACKGROUND

Transplantation of a graft organ or tissue from a donor to a host patient is a feature of certain medical procedures and treatment protocols. Despite efforts to avoid graft rejection through host-donor tissue type matching, in transplantation procedures where a donor organ is introduced into a host, immunosuppressive therapy is generally required to the maintain viability of the donor organ in the host. However, despite the wide use of immunosuppressive therapy, organ transplant rejection can occur.

Acute graft rejection (AR) of allograft tissue is a complex immune response that involves T-cell recognition of alloantigen in the allograft, co-stimulatory signals, elaboration of effector molecules by activated T cells, and an inflammatory response within the graft. Activation and recruitment of circulating leukocytes to the allograft is a central feature of this process. It is important to understand critical pathways regulated in AR, and if there are intrinsic similarities in the rejection molecular mechanisms across different solid organ transplants (e.g., kidney, heart, liver, lung, intestine, pancreas, etc.).

Early detection of AR is one of the major clinical concerns in the care of transplant recipients. Detection of AR before the onset of graft dysfunction allows successful treatment of this condition with aggressive immunosuppression. It is equally important to reduce immunosuppression in patients who do not have AR to minimize drug toxicity.

Accordingly, techniques for monitoring for an AR response in a transplant recipient, including predicting, diagnosing and characterizing AR, are of interest in the field. The present invention meets these and other needs.

SUMMARY OF THE INVENTION

Aspects of the present invention include methods for determining a transplant category of a subject having a transplant. Common mechanisms of rejection injury are uncovered across different tissue transplants, and provide a means to understand rational drug design. Various sources of tissues are examined form the patient for understanding AR mechanism (graft biopsy), as well as monitoring by minimal invasive means (blood) or non-invasive means (urine for the kidney allograft). For biomarker discovery different categories of markers are examined such as genes, proteins, peptides and antibodies. These biomarkers can help determine the subject's transplant category (e.g., acute allograft rejection (AR), stable allograft (STA), BK viremia, BK nephritis, drug toxicity or chronic allograft injury (CAI), and the like). Also provided are compositions, systems, kits and computer program products that find use in practicing the subject methods. The methods and compositions find use in a variety of applications.

In some embodiments, the invention provides methods for determining whether a subject who has received an allograft is undergoing an acute rejection (AR) response (or other graft injury, e.g., chronic allograft injury (CAI)), wherein the positive predictive value (PPV) is higher than 60, 70, 80, 90, 95, or 99.9%. In some embodiments, the invention provides methods for determining whether a subject who has received an allograft is undergoing AR response, wherein the PPV is equal or higher than 80%. In some embodiments, the invention provides methods for determining whether a subject who has received an allograft is undergoing an AR response, wherein the negative predictive value (NPV) is higher than 60, 70, 80, 90, 95, or 99.9%. In some embodiments, the invention provides methods for determining whether a subject who has received an allograft is undergoing an AR response, wherein the NPV is higher than 80%.

In some embodiments, the invention provides methods for determining whether a subject who has received an allograft is undergoing an AR response (or other graft injury, e.g., CAI), wherein the positive specificity is higher than 60, 70, 80, 90, 95, or 99.9%. In some embodiments, the invention provides methods for determining whether a subject who has received an allograft is undergoing AR response, wherein the specificity is equal or higher than 80%. In some embodiments, the invention provides methods for determining whether a subject who has received an allograft is undergoing an AR response, wherein the sensitivity is higher than 60, 70, 80, 90, 95, or 99.9%. In some embodiments, the invention provides methods for determining whether a subject who has received an allograft is undergoing an AR response, wherein the sensitivity is higher than 80%.

In some embodiments, the invention provides methods for determining whether a subject who has received an allograft is undergoing an AR response (or other graft injury, e.g., CAI) wherein the ROC value is higher than 60, 70, 80, 90, 95, or 99.9%. In some embodiments, the invention provides methods for determining whether a subject who has received an allograft is undergoing an AR response wherein the ROC value is higher than 70%. In some embodiments, the invention provides methods for determining whether a subject who has received an allograft is undergoing an AR response wherein the ROC value is higher than 80%. In some embodiments, the invention provides methods for determining whether a subject who has received an allograft is undergoing an AR response wherein the ROC value is higher than 90%.

In some embodiments, the p value in the analysis of the methods described herein is below 0.05, 04, 0.03, 0.02, 0.01, 0.009, 0.005, or 0.001. In some embodiments, the p value is below 0.001. Thus in some embodiments, the invention provides methods for determining whether a subject who has received an allograft is undergoing an AR response wherein the p value is below 0.05, 04, 0.03, 0.02, 0.01, 0.009, 0.005, or 0.001. In some embodiments, the p value is below 0.001. In some embodiments, the invention provides methods for determining whether a subject who has received an allograft is undergoing an AR response wherein the AUC value is higher than 0.5, 0.6, 07, 0.8 or 0.9. In some embodiments, the invention provides methods for determining whether a subject who has received an allograft is undergoing an AR response wherein the AUC value is higher than 0.7. In some embodiments, the invention provides methods for determining whether a subject who has received an allograft is undergoing an AR response wherein the AUC value is higher than 0.8. In some embodiments, the invention provides methods for determining whether a subject who has received an allograft is undergoing an AR response wherein the AUC value is higher than 0.9.

DEFINITIONS

For convenience, certain terms employed in the specification, examples, and appended claims are collected here.

"Acute rejection or AR" is the rejection by the immune system of a tissue transplant recipient when the transplanted tissue is immunologically foreign. Acute rejection is characterized by infiltration of the transplanted tissue by immune cells of the recipient, which carry out their effector function and destroy the transplanted tissue. The onset of acute rejection is rapid and generally occurs in humans within a few weeks after transplant surgery. Generally, acute rejection can be inhibited or suppressed with immunosuppressive drugs such as rapamycin, cyclosporin A, anti-CD40L monoclonal antibody and the like.

"Chronic transplant rejection or injury" or "CAI" generally occurs in humans within several months to years after engraftment, even in the presence of successful immunosuppression of acute rejection. Fibrosis is a common factor in chronic rejection of all types of organ transplants. Chronic rejection can typically be described by a range of specific disorders that are characteristic of the particular organ. For example, in lung transplants, such disorders include fibroproliferative destruction of the airway (bronchiolitis obliterans); in heart transplants or transplants of cardiac tissue, such as valve replacements, such disorders include fibrotic atherosclerosis; in kidney transplants, such disorders include, obstructive nephropathy, nephrosclerorsis, tubulointerstitial nephropathy; and in liver transplants, such disorders include disappearing bile duct syndrome. Chronic rejection can also be characterized by ischemic insult, denervation of the transplanted tissue, hyperlipidemia and hypertension associated with immunosuppressive drugs.

The term "transplant rejection" encompasses both acute and chronic transplant rejection. The term "transplant injury" refers to all manners of graft dysfunction, irrespective of pathological diagnosis. The term "organ injury" refers to biomarkers that track with poor function of the organ, irrespective of the organ being native or a transplant, and irrespective of the etiology.

The term "stringent assay conditions" as used herein refers to conditions that are compatible to produce binding pairs of proteins, peptides, antibodies and nucleic acids, e.g., surface bound and solution phase nucleic acids, of sufficient complementarity to provide for the desired level of specificity in the assay while being less compatible to the formation of binding pairs between binding members of insufficient complementarity to provide for the desired specificity. Stringent assay conditions are the summation or combination (totality) of both hybridization and wash conditions, as well as the combined prediction of the etiology of injury as inferred by the performance of a minimally invasive or non-invasive marker, with defined values for PPV, NPV, specificity and sensitivity.

"Stringent hybridization conditions" and "stringent hybridization wash conditions" in the context of nucleic acid hybridization (e.g., as in array, Southern or Northern hybridizations) are sequence dependent, and are different under different experimental parameters. Stringent hybridization conditions that can be used to identify nucleic acids within the scope of the invention can include, e.g., hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. Exemplary stringent hybridization conditions can also include hybridization in a buffer of 40% formamide, 1 M NaCl, and 1% SDS at 37° C., and a wash in 1×SSC at 45° C. Alternatively, hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C. can be employed. Yet additional stringent hybridization conditions include hybridization at 60° C. or higher and 3×SSC (450 mM sodium chloride/45 mM sodium citrate) or incubation at 42° C. in a solution containing 30% formamide, 1M NaCl, 0.5% sodium sarcosine, 50 mM MES, pH 6.5. Those of ordinary skill will readily recognize that alternative but comparable hybridization and wash conditions can be utilized to provide conditions of similar stringency.

In certain embodiments, the stringency of the wash conditions that set forth the conditions which determine whether a nucleic acid is specifically hybridized to a surface bound nucleic acid or a fluorphore labeled target. Wash conditions used to identify nucleic acids may include, e.g.: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions. Stringent conditions for washing can also be, e.g., 0.2×SSC/0.1% SDS at 42° C.

A specific example of stringent assay conditions is rotating hybridization at 65° C. in a salt based hybridization buffer with a total monovalent cation concentration of 1.5 M (e.g., as described in U.S. patent application Ser. No. 09/655,482 filed on Sep. 5, 2000, the disclosure of which is herein incorporated by reference) followed by washes of 0.5×SSC and 0.1×SSC at room temperature.

Stringent assay conditions are hybridization conditions that are at least as stringent as the above representative conditions, where a given set of conditions are considered to be at least as stringent if substantially no additional binding complexes that lack sufficient complementarity to provide for the desired specificity are produced in the given set of conditions as compared to the above specific conditions, where by "substantially no more" is meant less than about 5-fold more, typically less than about 3-fold more. Other stringent hybridization conditions are known in the art and may also be employed, as appropriate.

As used herein, the term "gene" or "recombinant gene" refers to a nucleic acid comprising an open reading frame encoding a polypeptide, including exon and (optionally) intron sequences. The term "intron" refers to a DNA sequence present in a given gene that is not translated into protein and is generally found between exons in a DNA molecule. In addition, a gene may optionally include its natural promoter (i.e., the promoter with which the exons and introns of the gene are operably linked in a non-recombinant cell, i.e., a naturally occurring cell), and associated regulatory sequences, and may or may not have sequences upstream of the AUG start site, and may or may not include untranslated leader sequences, signal sequences, downstream untranslated sequences, transcriptional start and stop sequences, polyadenylation signals, translational start and stop sequences, ribosome binding sites, and the like.

A "protein coding sequence" or a sequence that "encodes" a particular polypeptide or peptide, is a nucleic acid sequence that is transcribed (in the case of DNA) and is translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, cDNA from viral, procaryotic or eukaryotic mRNA, genomic DNA sequences from viral, procaryotic or eukaryotic DNA, and even synthetic DNA sequences. A transcription termination sequence may be located 3' to the coding sequence.

The terms "reference" and "control" are used interchangeably to refer to a known value or set of known values against which an observed value may be compared. As used herein, known means that the value represents an understood parameter, e.g., a level of expression of a marker gene in a graft survival or loss phenotype. A reference or control value may be from a single measurement or data point or may be a value calculated based on more than one measurement or data point (e.g., an average of many different measurements). Any convenient reference or control value(s) may be employed in practicing aspects of the subject invention.

The term "nucleic acid" includes DNA, RNA (double-stranded or single stranded), analogs (e.g., PNA or LNA molecules) and derivatives thereof. The terms "ribonucleic acid" and "RNA" as used herein mean a polymer composed of ribonucleotides. The terms "deoxyribonucleic acid" and "DNA" as used herein mean a polymer composed of deoxyribonucleotides. The term "mRNA" means messenger RNA. An "oligonucleotide" generally refers to a nucleotide multimer of about 10 to 100 nucleotides in length, while a "polynucleotide" includes a nucleotide multimer having any number of nucleotides.

The terms "protein", "polypeptide", "peptide" and the like refer to a polymer of amino acids (an amino acid sequence) and does not refer to a specific length of the molecule. This term also refers to or includes any modifications of the polypeptide (e.g., post-translational), such as glycosylations, acetylations, phosphorylations and the like. Included within the definition are, for example, polypeptides containing one or more analogs of an amino acid, polypeptides with substituted linkages, as well as other modifications known in the art, both naturally occurring and non-naturally occurring.

The term "assessing" and "evaluating" are used interchangeably to refer to any form of measurement, and includes determining if an element is present or not. The terms "determining," "measuring," "assessing," and "assaying" are used interchangeably and include both quantitative and qualitative determinations. Assessing may be relative or absolute. "Assessing the presence of" includes determining the amount of something present, as well as determining whether it is present or absent.

The terms "profile" and "signature" and "result" and "data", and the like, when used to describe peptide level or gene expression level data are used interchangeably (e.g., peptide signature/profile/result/data, gene expression signature/profile/result/data, etc.).

Certain abbreviations employed in this application include the following:
AR: Acute Rejection;
FDR: false discovery rate;
HC: Healthy control (e.g., a non-transplant recipient);
HPLC: high performance liquid chromatography;
LC: Liquid chromatography (e.g., HPLC);
LC-MS: Liquid chromatography and mass spectroscopy;
LC-MALDI: Liquid chromatography and matrix-assisted laser desorption ionization;
MALDI: matrix-assisted laser desorption ionization;
MS: mass spectroscopy
MRM: multiple reaction monitoring
NS: non-specific proteinuria with native renal diseases; nephrotic syndrome;
PBL: Peripheral Blood Leukocytes;
Q-PCR: quantitative real time polymerase chain reaction;
STA: stable allograft;
WBC: White blood cell.

BRIEF DESCRIPTION OF THE FIGURES

FIGS. 1A, 1B, 1C, and 1D: (A) Plot comparing FDR adjusted p-value (Y axis) and pooled standardized mean difference (log 2 scale) of gene expression data from solid organ transplant biopsy tissue. (B) Shows regulatory network that is activated during AR based on the gene expression profiling data from solid organ transplant biopsy tissue (see Table 1 below). (C) Shows log(p-value) for the 180 genes identified as significantly upregulated in gene expression data from solid organ transplant biopsy tissue split based on gene category (listed on the left). Bars indicate the p-value of the specific genes and the line represents the ratio. (D) Shows a table of the number of tissue specific genes overexpressed in solid organ transplant biopsy tissue, P-values, and FDR values.

DESCRIPTION OF THE SPECIFIC EMBODIMENTS

Figure 1A:
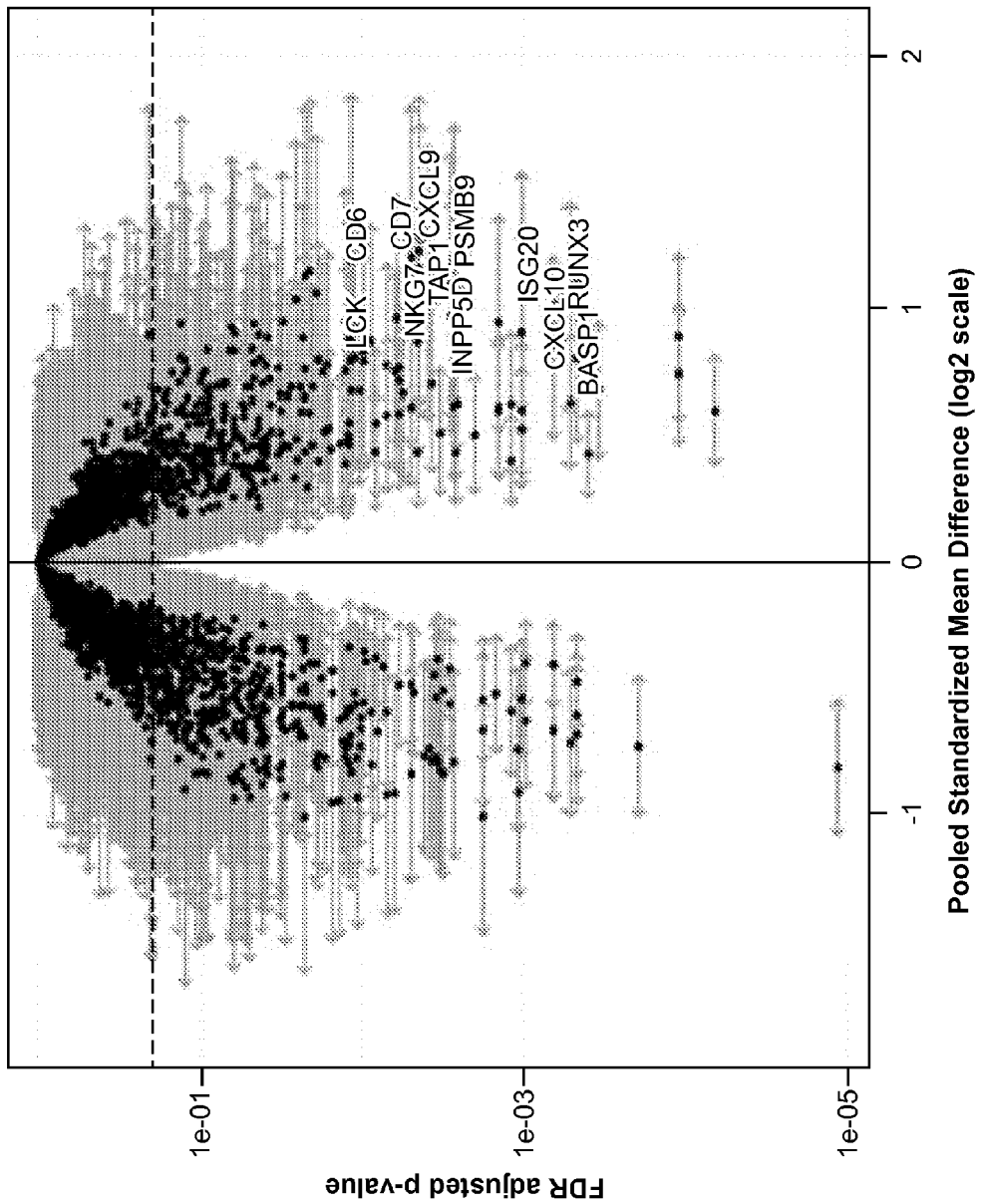

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Aspects of the subject invention provide methods for determining a clinical transplant category of a subject who has received an organ transplant. Increased adoption of transcriptional profiling of transplant biopsies has provided useful insights into the allograft injury mechanisms such as acute rejection (AR) and chronic allograft injury (CAI). As a result of these insights, it has been hypothesized that there is a common rejection mechanism across all transplanted solid organs (Wang et al., Trends in Immunology, v. 29, Issue 6, June 2008, Pages 256-262), as identified also recently by our group, whereby serum biomarkers that identify AR in both renal and cardiac transplants with high specificity and sensitivity (Chen, et al., 2010 PLOS v. 6 (9), e1000940). Identification of such a common rejection mechanism can lead to long-term benefits. For instance, it can facilitate novel diagnostics and therapeutics without requiring the understanding of individual tissue-specific injury.

We developed a novel method for meta-analysis of gene expression profiles from biopsy tissue from transplanted solid organ transplants to find common pathways regulated in AR, regardless of tissue source. Our method combines two types of evidences: (1) amount of change in expression across all studies (meta effect size) and (2) statistical significance of change in each study (meta p-value). We downloaded eight data sets from public domain corresponding to heart, lung, liver and kidney. Each data set was manually curated for quality control. We identified 180 significantly over-expressed genes across all data sets using meta effect size, and 1772 genes using meta p-value. There were 102 genes that were significant by both methods (Table 1).

TABLE 1

| | | | | | | | | | | |
|---|---|---|---|---|---|---|---|---|---|---|
| 102 common pathways regulated genes across all solid organ transplant AR ||||||||||||
| | | Combined Effect Sizes |||| Combined P-values |||||
| Gene Symbol | No. of Studies | Meta Effect Size | Meta Effect Size (Std. Error) | P-value | FDR | F-statistic (up) | P-value (up) | FDR (up) | F-statistic (down) | P-value (down) | FDR (down) |
|---|---|---|---|---|---|---|---|---|---|---|---|
| CXCL9 | 8 | 1.229 | 0.312 | 8.26E-05 | 1.35E-02 | 53.847 | 5.49E-06 | 6.58E-01 | 1.000 | 4.61E-03 | 1.00E+00 |
| CD7 | 8 | 1.201 | 0.309 | 0.000104 | 1.55E-02 | 68.901 | 1.55E-08 | 9.45E-01 | 1.000 | 2.94E-05 | 1.00E+00 |
| CORO1A | 8 | 1.192 | 0.335 | 0.000376 | 3.60E-02 | 63.857 | 1.16E-07 | 1.12E+00 | 1.000 | 1.64E-04 | 1.00E+00 |
| PSMB9 | 8 | 1.175 | 0.283 | 3.34E-05 | 7.79E-03 | 61.270 | 3.19E-07 | 8.51E-02 | 1.000 | 3.88E-04 | 1.00E+00 |
| NKG7 | 8 | 1.158 | 0.294 | 8.29E-05 | 1.35E-02 | 57.689 | 1.28E-06 | 1.72E+00 | 1.000 | 1.39E-03 | 1.00E+00 |
| ARPC1B | 8 | 1.149 | 0.349 | 0.001001 | 6.39E-02 | 52.732 | 8.34E-06 | 4.24E-04 | 1.000 | 6.26E-03 | 1.00E+00 |
| CD2 | 8 | 1.130 | 0.346 | 0.001097 | 6.77E-02 | 64.395 | 9.36E-08 | 9.75E-01 | 1.000 | 1.37E-04 | 1.00E+00 |
| TAP1 | 8 | 1.103 | 0.277 | 6.94E-05 | 1.17E-02 | 55.928 | 2.50E-06 | 4.90E-01 | 1.000 | 2.47E-03 | 1.00E+00 |
| INPP5D | 8 | 1.095 | 0.266 | 3.92E-05 | 8.51E-03 | 71.588 | 5.25E-09 | 4.24E-04 | 1.000 | 1.22E-05 | 1.00E+00 |
| ISG20 | 8 | 1.073 | 0.238 | 6.69E-06 | 2.65E-03 | 57.863 | 1.19E-06 | 4.24E-04 | 1.000 | 1.33E-03 | 1.00E+00 |
| BATF | 8 | 1.061 | 0.319 | 0.000874 | 5.87E-02 | 55.916 | 2.51E-06 | 9.26E-02 | 1.000 | 2.47E-03 | 1.00E+00 |
| PTPRCAP | 8 | 1.035 | 0.324 | 0.001424 | 7.86E-02 | 57.262 | 1.50E-06 | 3.42E-01 | 1.000 | 1.57E-03 | 1.00E+00 |
| RUNX3 | 8 | 1.006 | 0.212 | 2.12E-06 | 1.19E-03 | 41.157 | 0.000526 | 2.25E-01 | 1.000 | 1.62E-01 | 1.00E+00 |
| GZMK | 8 | 1.001 | 0.242 | 3.41E-05 | 7.88E-03 | 45.118 | 0.000133 | 4.24E-04 | 1.000 | 5.57E-02 | 1.00E+00 |
| ZAP70 | 8 | 0.968 | 0.235 | 3.67E-05 | 8.22E-03 | 54.265 | 4.69E-06 | 1.97E+00 | 1.000 | 4.08E-03 | 1.00E+00 |
| ARHGAP4 | 8 | 0.960 | 0.252 | 0.000142 | 1.92E-02 | 42.045 | 0.000389 | 2.96E-01 | 1.000 | 1.28E-01 | 1.00E+00 |
| IRF3 | 8 | 0.946 | 0.304 | 0.001843 | 9.18E-02 | 46.325 | 8.67E-05 | 4.24E-04 | 1.000 | 4.03E-02 | 1.00E+00 |
| GZMA | 8 | 0.945 | 0.270 | 0.000461 | 4.04E-02 | 40.402 | 0.00068 | 2.25E+00 | 1.000 | 1.92E-01 | 1.00E+00 |
| UCP2 | 8 | 0.944 | 0.217 | 1.32E-05 | 3.96E-03 | 38.571 | 0.001254 | 4.24E-04 | 1.000 | 2.86E-01 | 1.00E+00 |
| CD3D | 8 | 0.941 | 0.242 | 9.92E-05 | 1.53E-02 | 35.819 | 0.003066 | 5.34E-01 | 1.000 | 5.34E-01 | 1.00E+00 |
| HLA-DMA | 8 | 0.939 | 0.326 | 0.003944 | 1.38E-01 | 51.744 | 1.20E-05 | 8.60E-01 | 1.000 | 8.54E-03 | 1.00E+00 |
| LGALS9 | 8 | 0.927 | 0.344 | 0.006984 | 1.84E-01 | 45.441 | 0.000119 | 1.15E+00 | 1.000 | 5.32E-02 | 1.00E+00 |
| CD53 | 8 | 0.904 | 0.201 | 7.02E-06 | 2.76E-03 | 35.002 | 0.003971 | 4.24E-04 | 1.000 | 6.28E-01 | 1.00E+00 |
| ARHGDIB | 8 | 0.904 | 0.331 | 0.006314 | 1.76E-01 | 53.039 | 7.43E-06 | 1.65E+00 | 1.000 | 5.75E-03 | 1.00E+00 |
| C1orf38 | 8 | 0.895 | 0.305 | 0.003375 | 1.28E-01 | 43.272 | 0.000254 | 7.99E-01 | 1.000 | 9.34E-02 | 1.00E+00 |
| ITGB7 | 8 | 0.888 | 0.169 | 1.43E-07 | 1.57E-04 | 33.970 | 0.005485 | 4.24E-04 | 1.000 | 7.69E-01 | 1.00E+00 |
| MAP4K1 | 8 | 0.885 | 0.273 | 0.001196 | 7.10E-02 | 52.749 | 8.29E-06 | 3.02E+00 | 1.000 | 6.26E-03 | 1.00E+00 |
| STAT1 | 8 | 0.885 | 0.294 | 0.002624 | 1.12E-01 | 59.812 | 5.63E-07 | 3.23E+00 | 1.000 | 6.53E-04 | 1.00E+00 |
| MCM5 | 8 | 0.876 | 0.248 | 0.000402 | 3.76E-02 | 36.392 | 0.002551 | 4.24E-04 | 1.000 | 4.79E-01 | 1.00E+00 |
| CD8A | 8 | 0.870 | 0.237 | 0.000238 | 2.69E-02 | 34.414 | 0.004776 | 4.24E-04 | 1.000 | 7.07E-01 | 1.00E+00 |
| STAB1 | 8 | 0.868 | 0.221 | 8.69E-05 | 1.38E-02 | 41.085 | 0.000539 | 8.53E-01 | 1.000 | 1.62E-01 | 1.00E+00 |
| LCK | 8 | 0.862 | 0.242 | 0.000358 | 3.49E-02 | 54.433 | 4.41E-06 | 1.45E+01 | 0.563 | 3.95E-03 | 1.00E+00 |
| CXCL10 | 8 | 0.848 | 0.182 | 3.36E-06 | 1.60E-03 | 32.039 | 0.009883 | 6.45E-01 | 1.000 | 1.00E+00 | 1.00E+00 |
| TNFRSF14 | 8 | 0.840 | 0.201 | 2.90E-05 | 7.09E-03 | 30.426 | 0.015915 | 4.24E-04 | 1.000 | 1.00E+00 | 1.00E+00 |
| HCP5 | 8 | 0.838 | 0.293 | 0.004158 | 1.42E-01 | 39.859 | 0.000816 | 1.88E+00 | 1.000 | 2.15E-01 | 1.00E+00 |
| ITGB2 | 8 | 0.833 | 0.310 | 0.007245 | 1.88E-01 | 45.578 | 0.000113 | 2.30E+00 | 1.000 | 5.14E-02 | 1.00E+00 |
| CD14 | 8 | 0.832 | 0.305 | 0.006381 | 1.77E-01 | 43.655 | 0.000222 | 1.44E+00 | 1.000 | 8.42E-02 | 1.00E+00 |
| IL2RB | 8 | 0.829 | 0.228 | 0.00028 | 3.01E-02 | 29.630 | 0.02002 | 8.86E-01 | 1.000 | 1.00E+00 | 1.00E+00 |
| HLA-F | 8 | 0.807 | 0.225 | 0.000345 | 3.43E-02 | 51.399 | 1.37E-05 | 2.56E+00 | 1.000 | 9.32E-03 | 1.00E+00 |
| BASP1 | 8 | 0.804 | 0.167 | 1.56E-06 | 9.35E-04 | 30.693 | 0.014722 | 3.48E-01 | 1.000 | 1.00E+00 | 1.00E+00 |
| PLCB2 | 8 | 0.804 | 0.273 | 0.003267 | 1.26E-01 | 42.496 | 0.000333 | 8.53E-01 | 1.000 | 1.12E-01 | 1.00E+00 |
| CASP4 | 8 | 0.798 | 0.239 | 0.000824 | 5.68E-02 | 35.772 | 0.00311 | 5.36E-01 | 1.000 | 5.39E-01 | 1.00E+00 |
| LEF1 | 8 | 0.798 | 0.238 | 0.000807 | 5.64E-02 | 36.687 | 0.00232 | 1.56E+00 | 1.000 | 4.45E-01 | 1.00E+00 |
| IL10RA | 8 | 0.795 | 0.224 | 0.00039 | 3.68E-02 | 35.849 | 0.003036 | 1.69E-01 | 1.000 | 5.33E-01 | 1.00E+00 |
| TNFRSF9 | 8 | 0.791 | 0.217 | 0.000275 | 2.97E-02 | 26.157 | 0.051864 | 2.92E-02 | 1.000 | 1.00E+00 | 1.00E+00 |
| FCER1G | 8 | 0.782 | 0.271 | 0.00395 | 1.38E-01 | 35.161 | 0.003777 | 1.88E+00 | 1.000 | 6.10E-01 | 1.00E+00 |
| FOXM1 | 8 | 0.778 | 0.229 | 0.000665 | 4.98E-02 | 22.084 | 0.1405 | 1.04E-01 | 1.000 | 1.00E+00 | 1.00E+00 |
| BIRC5 | 8 | 0.776 | 0.207 | 0.000175 | 2.22E-02 | 40.910 | 0.000572 | 1.16E+00 | 1.000 | 1.70E-01 | 1.00E+00 |
| MMP9 | 8 | 0.775 | 0.259 | 0.002778 | 1.15E-01 | 35.180 | 0.003755 | 6.42E-01 | 1.000 | 6.09E-01 | 1.00E+00 |
| F13A1 | 8 | 0.766 | 0.200 | 0.000132 | 1.83E-02 | 30.632 | 0.01499 | 4.24E-04 | 1.000 | 1.00E+00 | 1.00E+00 |
| MDK | 8 | 0.765 | 0.249 | 0.002154 | 9.94E-02 | 26.177 | 0.051586 | 2.42E+00 | 1.000 | 1.00E+00 | 1.00E+00 |
| GBP2 | 8 | 0.762 | 0.234 | 0.001121 | 6.84E-02 | 27.116 | 0.040211 | 1.03E+00 | 1.000 | 1.00E+00 | 1.00E+00 |
| CD6 | 8 | 0.753 | 0.215 | 0.000464 | 4.04E-02 | 39.122 | 0.001044 | 2.07E+00 | 1.000 | 2.55E-01 | 1.00E+00 |
| TNFRSF1B | 8 | 0.751 | 0.198 | 0.000147 | 1.98E-02 | 28.529 | 0.026782 | 5.70E-01 | 1.000 | 1.00E+00 | 1.00E+00 |
| TNFRSF1A | 8 | 0.749 | 0.222 | 0.000731 | 5.32E-02 | 26.312 | 0.049799 | 5.94E-01 | 1.000 | 1.00E+00 | 1.00E+00 |
| AIM2 | 8 | 0.743 | 0.142 | 1.55E-07 | 1.65E-04 | 25.794 | 0.056994 | 4.24E-04 | 1.000 | 1.00E+00 | 1.00E+00 |
| IL15RA | 8 | 0.736 | 0.138 | 9.45E-08 | 1.19E-04 | 33.091 | 0.007187 | 2.13E+00 | 1.000 | 9.34E-01 | 1.00E+00 |
| CDC20 | 8 | 0.723 | 0.251 | 0.003916 | 1.38E-01 | 22.419 | 0.130169 | 5.73E-01 | 1.000 | 1.00E+00 | 1.00E+00 |
| IRF1 | 8 | 0.719 | 0.238 | 0.002481 | 1.08E-01 | 29.262 | 0.022481 | 2.46E+00 | 1.000 | 1.00E+00 | 1.00E+00 |
| STK10 | 8 | 0.716 | 0.187 | 0.000134 | 1.84E-02 | 31.919 | 0.010244 | 4.24E-04 | 1.000 | 1.00E+00 | 1.00E+00 |
| CD48 | 8 | 0.708 | 0.266 | 0.007784 | 1.95E-01 | 25.220 | 0.066041 | 1.63E+00 | 1.000 | 1.00E+00 | 1.00E+00 |
| TNF | 8 | 0.704 | 0.237 | 0.002968 | 1.20E-01 | 31.268 | 0.012433 | 2.41E+00 | 1.000 | 1.00E+00 | 1.00E+00 |
| ATF5 | 8 | 0.701 | 0.175 | 6.26E-05 | 1.11E-02 | 36.291 | 0.002636 | 6.27E-01 | 1.000 | 4.88E-01 | 1.00E+00 |
| IKBKE | 8 | 0.691 | 0.242 | 0.004354 | 1.45E-01 | 31.706 | 0.010918 | 1.22E+00 | 1.000 | 1.00E+00 | 1.00E+00 |
| PLEK | 8 | 0.690 | 0.218 | 0.001566 | 8.35E-02 | 27.884 | 0.032647 | 4.19E-01 | 1.000 | 1.00E+00 | 1.00E+00 |
| ADAM8 | 8 | 0.689 | 0.214 | 0.001282 | 7.36E-02 | 35.151 | 0.003789 | 8.53E-01 | 1.000 | 6.10E-01 | 1.00E+00 |
| HLA-G | 8 | 0.679 | 0.137 | 6.81E-07 | 5.35E-04 | 32.896 | 0.007628 | 4.24E-04 | 1.000 | 9.71E-01 | 1.00E+00 |
| SH2D2A | 8 | 0.676 | 0.190 | 0.000375 | 3.60E-02 | 23.935 | 0.090924 | 1.01E+00 | 1.000 | 1.00E+00 | 1.00E+00 |
| RGS10 | 8 | 0.674 | 0.187 | 0.000305 | 3.18E-02 | 31.568 | 0.011376 | 8.53E-01 | 1.000 | 1.00E+00 | 1.00E+00 |
| BTN3A2 | 8 | 0.667 | 0.173 | 0.00012 | 1.71E-02 | 28.853 | 0.024945 | 2.34E+00 | 1.000 | 1.00E+00 | 1.00E+00 |
| DDB2 | 8 | 0.661 | 0.215 | 0.002064 | 9.69E-02 | 21.512 | 0.159646 | 4.24E-04 | 1.000 | 1.00E+00 | 1.00E+00 |
| HLA-A | 8 | 0.656 | 0.209 | 0.001674 | 8.70E-02 | 31.862 | 0.010422 | 1.52E+00 | 1.000 | 1.00E+00 | 1.00E+00 |

TABLE 1-continued 102 common pathways regulated genes across all solid organ transplant AR

| | | Combined Effect Sizes | | | | Combined P-values | | | | |
|---|---|---|---|---|---|---|---|---|---|---|
| Gene Symbol | No. of Studies | Meta Effect Size | Meta Effect Size (Std. Error) | P-value | FDR | F-statistic (up) | P-value (up) | FDR (up) | F-statistic (down) | P-value (down) | FDR (down) |
| HLA-E | 8 | 0.652 | 0.201 | 0.001153 | 6.94E−02 | 36.028 | 0.002868 | 1.67E+00 | 1.000 | 5.14E−01 | 1.00E+00 |
| AIF1 | 8 | 0.637 | 0.222 | 0.004096 | 1.41E−01 | 30.397 | 0.01605 | 1.03E+00 | 1.000 | 1.00E+00 | 1.00E+00 |
| IFITM3 | 8 | 0.633 | 0.134 | 2.19E−06 | 1.20E−03 | 24.210 | 0.085024 | 8.70E−01 | 1.000 | 1.00E+00 | 1.00E+00 |
| PTPRC | 8 | 0.627 | 0.226 | 0.005395 | 1.62E−01 | 31.976 | 0.010071 | 3.53E+00 | 1.000 | 1.00E+00 | 1.00E+00 |
| MAN2B1 | 8 | 0.625 | 0.236 | 0.008117 | 1.99E−01 | 22.819 | 0.11866 | 9.47E−01 | 1.000 | 1.00E+00 | 1.00E+00 |
| DDX23 | 8 | 0.624 | 0.206 | 0.002394 | 1.06E−01 | 26.682 | 0.045157 | 6.91E−01 | 1.000 | 1.00E+00 | 1.00E+00 |
| MARCKS | 8 | 0.616 | 0.141 | 1.34E−05 | 3.99E−03 | 23.679 | 0.096749 | 3.09E+00 | 1.000 | 1.00E+00 | 1.00E+00 |
| PSME1 | 8 | 0.615 | 0.219 | 0.004918 | 1.55E−01 | 21.765 | 0.150949 | 7.10E−01 | 1.000 | 1.00E+00 | 1.00E+00 |
| HLA-DQB1 | 8 | 0.601 | 0.194 | 0.001989 | 9.55E−02 | 37.930 | 0.001548 | 1.14E+01 | 0.786 | 3.34E−01 | 1.00E+00 |
| RAB27A | 8 | 0.601 | 0.109 | 3.70E−08 | 6.30E−05 | 22.793 | 0.119394 | 5.36E−02 | 1.000 | 1.00E+00 | 1.00E+00 |
| BBC3 | 8 | 0.597 | 0.185 | 0.001249 | 7.27E−02 | 22.702 | 0.121927 | 2.92E+00 | 1.000 | 1.00E+00 | 1.00E+00 |
| POLR2A | 8 | 0.594 | 0.224 | 0.007933 | 1.97E−01 | 31.439 | 0.011821 | 1.65E+00 | 1.000 | 1.00E+00 | 1.00E+00 |
| ADAM19 | 8 | 0.593 | 0.180 | 0.001003 | 6.39E−02 | 25.667 | 0.0589 | 8.53E−01 | 1.000 | 1.00E+00 | 1.00E+00 |
| NELL2 | 8 | 0.580 | 0.207 | 0.005007 | 1.57E−01 | 20.796 | 0.186499 | 7.43E−02 | 1.000 | 1.00E+00 | 1.00E+00 |
| NNMT | 8 | 0.569 | 0.209 | 0.006481 | 1.78E−01 | 21.213 | 0.170483 | 7.99E−01 | 1.000 | 1.00E+00 | 1.00E+00 |
| NUP210 | 8 | 0.569 | 0.194 | 0.003416 | 1.29E−01 | 31.018 | 0.013383 | 8.53E−01 | 1.000 | 1.00E+00 | 1.00E+00 |
| VAMP5 | 8 | 0.533 | 0.156 | 0.000645 | 4.88E−02 | 21.575 | 0.157461 | 1.90E+00 | 1.000 | 1.00E+00 | 1.00E+00 |
| IRF4 | 8 | 0.523 | 0.192 | 0.006448 | 1.78E−01 | 28.682 | 0.026169 | 1.96E+00 | 1.000 | 1.00E+00 | 1.00E+00 |
| SERPINH1 | 8 | 0.514 | 0.166 | 0.002007 | 9.55E−02 | 32.862 | 0.007709 | 2.66E−01 | 1.000 | 9.73E−01 | 1.00E+00 |
| TNFAIP2 | 8 | 0.511 | 0.166 | 0.00201 | 9.55E−02 | 22.853 | 0.117733 | 2.01E+00 | 1.000 | 1.00E+00 | 1.00E+00 |
| MAP3K11 | 8 | 0.508 | 0.144 | 0.000436 | 3.91E−02 | 23.248 | 0.107276 | 3.97E+00 | 1.000 | 1.00E+00 | 1.00E+00 |
| PRKD2 | 8 | 0.496 | 0.141 | 0.000414 | 3.81E−02 | 20.921 | 0.181558 | 3.53E−01 | 1.000 | 1.00E+00 | 1.00E+00 |
| CCL13 | 8 | 0.482 | 0.172 | 0.005205 | 1.60E−01 | 21.718 | 0.152533 | 1.58E+00 | 1.000 | 1.00E+00 | 1.00E+00 |
| KRT17 | 8 | 0.468 | 0.174 | 0.007174 | 1.87E−01 | 22.769 | 0.120056 | 3.75E−01 | 1.000 | 1.00E+00 | 1.00E+00 |
| CD44 | 8 | 0.463 | 0.159 | 0.003532 | 1.31E−01 | 28.914 | 0.02452 | 3.14E+00 | 1.000 | 1.00E+00 | 1.00E+00 |
| DDX11 | 8 | 0.460 | 0.156 | 0.003309 | 1.27E−01 | 23.504 | 0.100901 | 2.19E+00 | 1.000 | 1.00E+00 | 1.00E+00 |
| ADAMTS3 | 8 | 0.458 | 0.153 | 0.00269 | 1.14E−01 | 51.134 | 1.51E−05 | 4.24E−04 | 1.000 | 1.01E−02 | 1.00E+00 |
| FZD2 | 8 | 0.449 | 0.145 | 0.001929 | 9.41E−02 | 21.433 | 0.162453 | 8.02E−01 | 1.000 | 1.00E+00 | 1.00E+00 |
| IRF5 | 8 | 0.438 | 0.148 | 0.003119 | 1.23E−01 | 21.568 | 0.157705 | 8.13E+00 | 0.945 | 1.00E+00 | 1.00E+00 |
| PML | 8 | 0.387 | 0.142 | 0.006573 | 1.79E−01 | 29.830 | 0.018906 | 4.21E+00 | 0.998 | 1.00E+00 | 1.00E+00 |

Figure 1B:
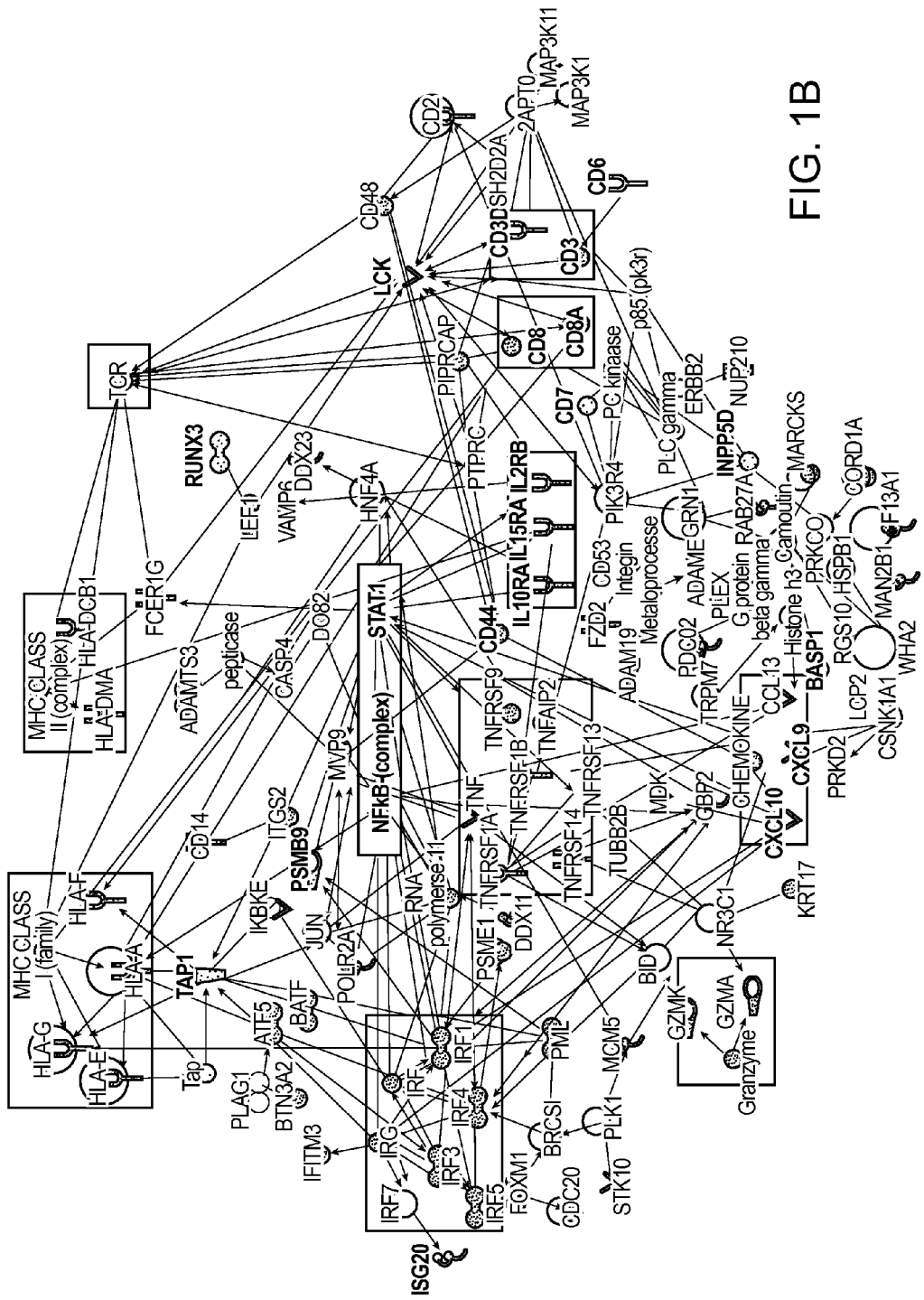
Figure 1C:
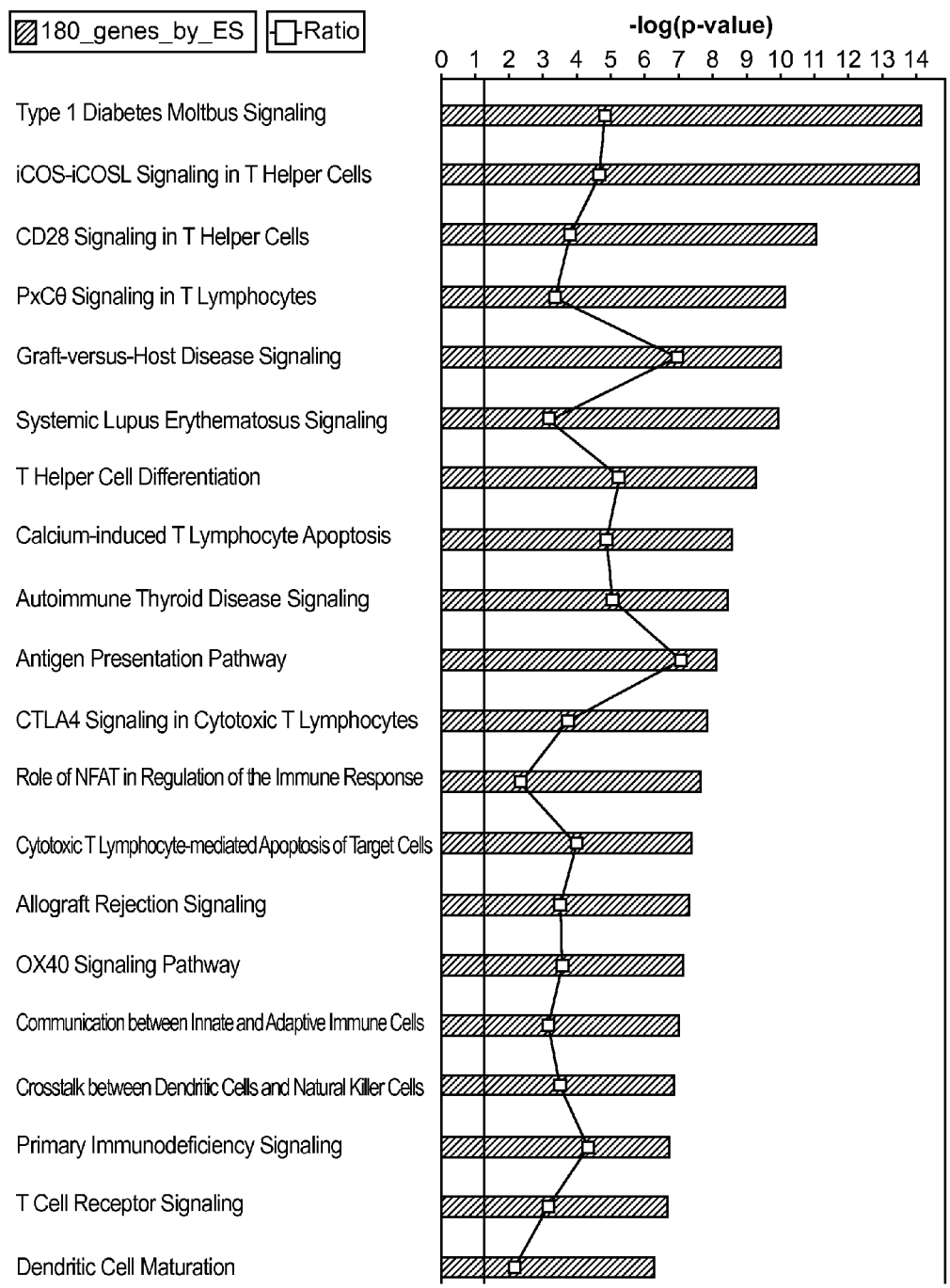

The 102 genes are significantly over expressed across all transplanted organs and form a single regulatory network that is activated during AR (the most relevant networks are shown in FIG. 1). We have shown two of the 102 genes (CD44 and CXCL9) can serve as non-invasive biomarkers for rejection in serum of a transplant patient with high specificity and sensitivity. The Pearson correlation coefficient of the most significant genes cross organ rejection shows strong correlation between many genes in this cluster. We further identified 12 genes, majority of which are regulated by a transcription factor STAT1. The 12 genes are BASP1, CD6, CD7, CXCL10, CXCL9, INPP5D, ISG20, LCK, NKG7, PSMB9, RUNX3, and TAP1. These genes are highly enriched for known drug targets. We further validated over-expression of these 12 genes in an independent cohort of 118 renal graft biopsies using DNA microarrays (n=101, AR=43) and RT-PCR (n=17, AR=8).

We next evaluated the use of peripheral blood as a source of diagnosis and predicting specific etiology of injury in the graft. We developed cell type-specific significance analysis of microarrays (csSAM or cell specific significance analysis of microarrays) for analyzing differential gene expression for each cell type in a biological sample (peripheral blood) from microarray data and relative cell-type frequencies. We applied this method to whole-blood gene expression datasets from kidney transplant recipients. Our results showed that csSAM identified hundreds of differentially expressed genes in monocytes, that were otherwise undetectable. Furthermore, monocytes-specific expression profile successfully allowed distinguishing between AR and STA groups in organ transplant recipients. In fact, the minimally invasive gene-set, for analysis by transcriptional analysis (e.g., QPCR), consists of a combination of the genes listed in Table 2, many of which are regulated by pSTAT, as determined by phosphoflow. Though all of these genes have been cross validated as highly specific (>80%) and sensitive (>80%) biomarkers for diagnosis and prediction of AR in pediatric and adult renal transplant recipients, 10 of the 23 genes are also highly specific (>80%) and sensitive (>80%) biomarkers for diagnosis and prediction of AR in adult heart transplant recipients.

TABLE 2

Peripheral Blood gene-sets for diagnosing and predicting solid organ transplant AR

| Gene ID | p values | fold change | Average AR | Average STA | Median AR | Median STA |
|---|---|---|---|---|---|---|
| DUSP1 | 0.004 | 2.2 | 3.1 | 1.41 | 2.11 | 1.05 |
| NAMPT | 0.07 | 1.68 | 2.36 | 1.41 | 1.71 | 1.09 |
| PSEN1 | 0.63 | 1.07 | 1.37 | 1.28 | 1.29 | 1.13 |
| MAPK9 | 0.01 | 1.49 | 1.97 | 1.33 | 1.73 | 1.1 |
| NKTR | 0.84 | 1.03 | 1.19 | 1.16 | 1.05 | 1.17 |
| RYBP | 0.1 | 1.24 | 1.51 | 1.21 | 1.43 | 1.13 |
| RNF130 | 0.01 | 1.56 | 1.96 | 1.25 | 1.85 | 1.15 |
| IFNGR1 | 0.01 | 1.94 | 6.58 | 3.38 | 5.51 | 2.57 |
| ITGAX | 0.01 | 1.9 | 2.51 | 1.32 | 1.79 | 1.18 |
| CFLAR | 0.002 | 1.98 | 5.12 | 2.58 | 4.32 | 1.98 |
| GBP2 | 0.01 | 1.49 | 2 | 1.34 | 1.68 | 1.12 |
| TNFRSF1A | 0.08 | 1.29 | 2.01 | 1.56 | 1.96 | 1.31 |
| MAP2K3 | 0.05 | 1.28 | 1.54 | 1.2 | 1.43 | 1.15 |
| EPOR | 0.003 | 1.56 | 1.7 | 1.08 | 1.62 | 0.91 |
| SLC25A37 | 0.001 | 1.73 | 2.47 | 1.42 | 2.28 | 1.13 |
| ANK1 | 0.06 | 1.24 | 1.41 | 1.13 | 1.31 | 1.04 |
| CHST11 | 0.001 | 1.8 | 2.14 | 1.19 | 1.79 | 1.06 |
| LYST | 0.08 | 1.17 | 1.44 | 1.23 | 1.34 | 1.15 |

TABLE 2-continued

Peripheral Blood gene-sets for diagnosing
and predicting solid organ transplant AR

| Gene ID | p values | fold change | Average AR | Average STA | Median AR | Median STA |
|---|---|---|---|---|---|---|
| RARA | 0.03 | 1.51 | 1.85 | 1.23 | 1.59 | 1.16 |
| PCTP | 0.0003 | 1.65 | 1.97 | 1.19 | 1.88 | 1.09 |
| ABTB1 | 0.01 | 1.56 | 1.9 | 1.22 | 1.49 | 1.01 |
| RXRA | 0.05 | 1.22 | 1.34 | 1.09 | 1.34 | 1.1 |
| B2M | 0.004 | 1.78 | 2.36 | 1.33 | 1.9 | 1.1 |

To use gene-sets for non-invasive diagnosis and prediction of AR, while controlling for BK viral infection (BK virus nephropathy or BKVN), we also evaluated urinary genes by qPCR. The genes to be tested in urine for rejection diagnosis were selected by three strategies: highly statistically significant genes (q scores<5% by statistical analysis of microarrays, and >2 fold change in rejection) from previously conducted microarray studies (Affymetrix HU133plus2.0) on 71 peripheral blood samples (44AR, 27 stable, STA), 51 kidney transplant biopsy samples (32 AR, 19 STA), and known urine-present genes obtained from data filtering in Ingenuity Pathway Analysis (Ingenuity). Two independent urine sample sets were selected for qPCR validation consists of 89 samples from patients with biopsy-proven AR (n=30), biopsy-proven stable grafts (STA n=40) and BK virus infection (BK n=19, with no AR). The extracted total RNA was then subjected to qPCR in 384-well plates using RT2 qPCR system (SuperArray). Primers were selected from cDNA sequences of the chosen genes using Primer 3.0, a web-based software. 26 genes were chosen from array data to run qPCR (12 from blood data, 15 from biopsy data, some of the genes known to be preset in urine). qPCR were carried in RT2 qPCR Master Mix (SuperArray). Relative gene expression levels of each gene were calculated using the comparative delta-CT method and normalized to 18S ribosomal RNA. All samples were tested in duplicates. Student T test was applied for statistical analysis. P<0.05 was considered significant. 5 of 19 genes were expressed significantly higher in AR as compared to STA samples (FCGR3A p=0.01; PRRX1 p=0.02; PRSS1 p=0.01; RNPS1 p=0.04 and TLR8 p=0.01). A logistic regression model was built using the 5-gene qPCR expression data from Validation Set 1, resulting a high specificity and sensitivity with ROC score of 93.8%. The model was fed with another independent set of 34 urine samples (Validation Set 2: 18AR, 16STA), and a high AR prediction score was achieved with a sensitivity of 80%, specificity of 89%, positive prediction value (PPV) of 75%, and a negative prediction value (NPV) of 86%. 15 BK samples were included in Validation Set 2. The expression of all 5 genes showed were significantly higher not only in AR samples compared to STA, but also in AR when compared to BK samples (FCGR3A p<0.001, PRRX1 p=0.001, PRSS1 p<0.001; RNPS1 p=0.001 and TLR8 p<0.03), confirming this 5 genes are indeed AR specific.

For bone marrow transplantation, similar approaches were undertaken to assemble a study to find gene-based biomarkers in peripheral blood that can diagnose and predict chronic Graft vs Host disease. Table 3 shows a list of 10 genes whose expression level can be used to determine a GvHD phenotype in a subject having an allogeneic HCT transplant. The gene expression levels of these 10 genes is significantly higher in a GvHD phenotype with respect to a nonGvHD phenotype (e.g., genes IL1R2, ADAMTS2, AREG, HRASLS, TPST1, IRS2, GPR30, KLF9, ZBTB16 and SESN1 are significantly up-regulated in GvHD as compared to a normal control or to non-GvHD transplant recipients). In certain embodiments, the gene expression level of gene IL1R2 can be used to determine a GvHD phenotype in a subject having an allogeneic HCT transplant.

TABLE 3

Ten predictive biomarkers of GvHD and nonGvHD

| Probe ID | Entrez GeneID | Gene Symbol | FDR (%) |
|---|---|---|---|
| A_23_P79398 | 7850 | IL1R2 | 0 |
| A_23_P321307 | 9509 | ADAMTS2 | 0 |
| A_23_P259071 | 374 | AREG | 2 |
| A_23_P57658 | 57110 | HRASLS | 0 |
| A_23_P145965 | 8460 | TPST1 | 0 |
| A_24_P154037 | 8660 | IRS2 | 0 |
| A_23_P8640 | 2852 | GPR30 | 0 |
| A_23_P415401 | 687 | KLF9 | 0 |
| A_23_P104804 | 7704 | ZBTB16 | 0 |
| A_23_P93562 | 27244 | SESN1 | 0 |

Figure 2A:
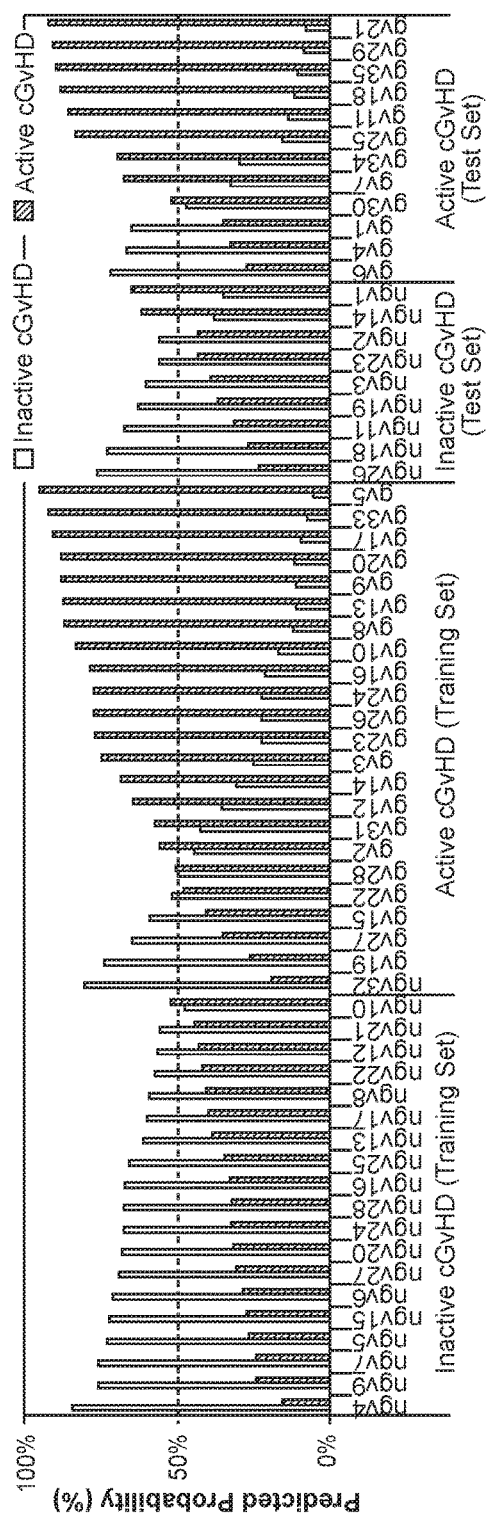
FIGS. 2A-2B illustrate cGvHD sample prediction based on a 10 gene-set. (A) 10 gene-set derived from comparison of randomly selected active cGvHD and inactive cGvHD samples in training set by Statistical Analysis Microarray and Predictive Analysis Microarray. Inactive cGvHD predictions are shown in grey color and active cGvHD predictions are shown in black color. (B) 10 gene-set prediction probabilities based on multinomial logistic regression model from cGvHD samples at the last follow-up.
Figure 2B:
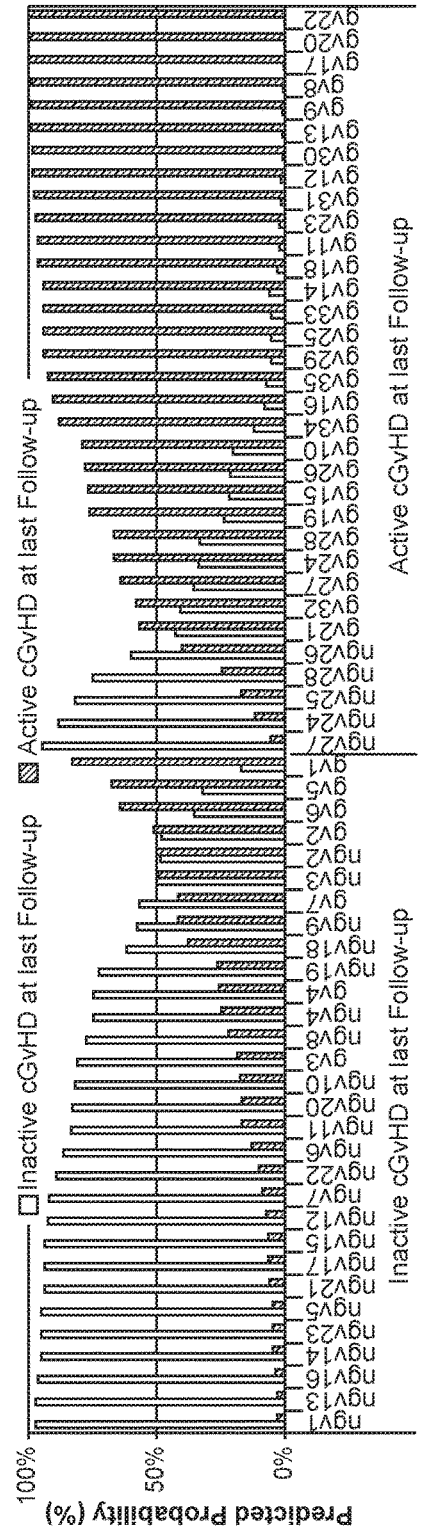

FIG. 2A shows a 10 gene-set derived from comparison of randomly selected active cGvHD and inactive cGvHD samples in training set (n=42; 19 inactive cGvHD and 23 active cGvHD) by Statistical Analysis Microarray and Predictive Analysis Microarray. Inactive cGvHD predictions were shown in grey color and active cGvHD predictions were shown in black color and predictions for samples in test set (n=21; 9 inactive cGvHD and 12 active cGvHD) were 75% sensitivity for active cGvHD, 78% specificity for inactive cGvHD, 82% PPV, and 70% NPV. FIG. 2B shows the 10 gene-set prediction probabilities based on multimomial logistic regression model from cGvHD samples at the last follow-up (30 inactive cGvHD and 33 active cGvHD at the last follow-up). The 10 gene-set model performed with 85% sensitivity, 83% specificity, 85% PPV, and 83% NPV.

In certain embodiments, the methods include obtaining a urine sample from the subject and determining the level of one or more peptides/proteins therein to obtain a protein or peptide signature of the sample. The protein signature can then be used to determine the clinical transplant category of the subject, e.g., by comparing to one or more protein signatures from subjects having a known transplant category (e.g., acute rejection (AR), stable graft function (STA), healthy control (HC), nephrotic syndrome (NS)). Such known protein signatures can also be called controls or reference signatures/profiles. Also provided are compositions, systems, kits and computer program products that find use in practicing the subject methods. In a study of urinary proteome analysis using shotgun proteomics approach, and bioinformatics data mining, a total of 92 urine samples were examined from 4 different clinical categories (AR, STA, NS, Healthy control) and ELISA validation performed on the 3 most significant urine proteins (CD44, UMOD and PEDF) on independent urine samples (Sigdel et al, PROTEMICS Clin. Appl, 2010). A total of 1446 urine proteins were found in normal urine. The significance threshold for positive ID for a urine protein in one phenotype was the presence of a minimum of 2 peptide fragments/protein in AR samples vs no peptides from that protein in STA and healthy control samples. The log based fold change was significant is >2 in one category (AR) vs the other category (non-AR). Tables 4A-4C show the most significant urine proteins in AR.

Table 4A to 4C

Proteins Specific to Acute Rejection

TABLE 4A

Proteins identified only in AR urine

| S. No. | IPI ID | Gene Symbol | Protein Name |
|---|---|---|---|
| 1 | IPI00103082.7 | HLA-DBP | HLA class II histocompatibility antigen, DP(W4) beta chain |
| 2 | IPI00005180.2 | IgHM | HLA class II histocompatibility antigen, DRB1-8 beta chain |
| 3 | IPI00021727.1 | C4BPA | C4b-binding protein alpha chain |
| 4 | IPI00641889.1 | KIAA1522 | 25 kDa protein |
| 5 | IPI00746396.1 | | 302 kDa protein |
| 6 | IPI00760688.2 | HLA-DR | MHC class II antigen (Fragment) |
| 7 | IPI00027255.1 | MYL6B | Myosin light chain 1, slow-twitch muscle A isoform |
| 8 | IPI00783351.1 | SUMF2 | sulfatase modifying factor 2 isoform d |
| 9 | IPI00743218.1 | HLA-DQB1 | HLA class II histocompatibility antigen, DQ(3) beta chain |

TABLE 4B

Quantitatively up-regulated urinary proteins in AR compared to STA

| S. No. | IPI ID | Gene Symbol | Protein Name | AR Spectral Counts | STA Spectral Count | Fold change (LOG2) |
|---|---|---|---|---|---|---|
| 1 | IPI00017601.1 | CP | Ceruloplasmin | 439 | 141 | 2 |
| 2 | IPI00032291.1 | C5 | Complement C5 | 26 | 8 | 2 |
| 3 | IPI00410714.4 | HBA1 | Hemoglobin subunit alpha | 30 | 9 | 2 |
| 4 | IPI00010858.1 | KLK3 | Prostate-specific antigen | 21 | 4 | 2 |
| 5 | IPI00303963.1 | C2 | Complement C2 | 12 | 4 | 2 |
| 6 | IPI00747314.1 | | 13 kDa protein | 15 | 4 | 2 |
| 7 | IPI00477804.2 | | Immunglobulin heavy chain variable region | 10 | 3 | 2 |
| 8 | IPI00464948.3 | HLA-DRA | major histocompatibility complex, class II, DR alpha | 10 | 1 | 3 |
| 9 | IPI00021304.1 | KRT2 | Keratin, type II cytoskeletal 2 epidermal | 5 | 1 | 2 |
| 10 | IPI00741163.1 | LOC65265 | PREDICTED: similar to Ig heavy chain V-II region ARH-77 | 6 | 2 | 2 |
| 11 | IPI00783393.1 | | Immunglobulin heavy chain variable region | 10 | 2 | 2 |
| 12 | IPI00745363.1 | LOC652113 | PREDICTED: similar to Ig heavy chain V-III region VH26 | 6 | 2 | 2 |
| 13 | IPI00386142.1 | | Ig heavy chain V-II region ARH-77 | 12 | 2 | 3 |
| 14 | IPI00737304.1 | LOC652141 | PREDICTED: similar to Ig heavy chain V-III region VH26 | 6 | 1 | 3 |
| 15 | IPI00556442.1 | IGFBP2 | Insulin-like growth factor binding protein 2 variant | 5 | 1 | 2 |
| 16 | IPI00736985.1 | LOC441368 | PREDICTED: similar to Ceruloplasmin | 21 | 5 | 2 |
| 17 | IPI00477540.2 | | 13 kDa protein | 9 | 3 | 2 |
| 18 | IPI00382540.1 | | Ig heavy chain V-II region NEWM | 11 | 2 | 2 |
| 19 | IPI00386135.1 | | Ig lambda chain V-VI region SUT | 4 | 1 | 2 |
| 20 | IPI00554676.1 | HBE1 | Hemoglobin subunit gamma-2 | 4 | 1 | 2 |
| 21 | IPI00387119.1 | | Ig kappa chain V-III region POM | 11 | 3 | 2 |
| 22 | IPI00419517.1 | IGHV1-69 | IGHV1-69 protein | 6 | 2 | 2 |

TABLE 4C

Quantitatively down-regulated urinary proteins in AR compared to STA

| S. No | IPI ID | Gene Symbol | Protein Name | AR Spectral Count | STA Spectral Count | Fold change (LOG2) |
|---|---|---|---|---|---|---|
| 1 | IPI00022426.1 | AMBP | AMBP protein | 724 | 2201 | 2 |
| 2 | IPI00160130.3 | CUBN | Cubilin | 59 | 209 | 2 |
| 3 | IPI00012503.1 | PSAP | Isoform Sapmu0 of Proactivator polypeptide | 93 | 427 | 2 |
| 4 | IPI00640271.1 | UMOD | Tamm-Horsefall Protein | 122 | 363 | 2 |
| 5 | IPI00745705.1 | AMY2A | Amylase, alpha 2A; pancreatic variant | 89 | 264 | 2 |
| 6 | IPI00744362.1 | FN1 | Hypothetical protein DKFZp686K08164 | 36 | 126 | 2 |
| 7 | IPI00021885.1 | FGA | Isoform 1 of Fibrinogen alpha chain | 60 | 176 | 2 |
| 8 | IPI00784458.1 | FBN1 | 312 kDa protein | 30 | 112 | 2 |
| 9 | IPI00000073.1 | EGF | Proepidermal growth factor | 37 | 140 | 2 |
| 10 | IPI00328113.2 | FBN1 | Fibrillin1 | 20 | 76 | 2 |

TABLE 4C-continued

Quantitatively down-regulated urinary proteins in AR compared to STA

| S. No | IPI ID | Gene Symbol | Protein Name | AR Spectral Count | STA Spectral Count | Fold change (LOG2) |
|---|---|---|---|---|---|---|
| 11 | IPI00744835.1 | PSAP | Isoform Sapmu9 of Proactivator polypeptide | 71 | 312 | 2 |
| 12 | IPI00641961.1 | COL12A1 | Collagen, type XII, alpha 1 | 39 | 128 | 2 |
| 13 | IPI00783446.1 | GAA | Lysosomal alphaglucosidase | 29 | 120 | 2 |
| 14 | IPI00329573.8 | COL12A1 | Isoform Long of Collagen alpha1(XII) chain | 32 | 117 | 2 |
| 15 | IPI00023673.1 | LGALS3BP | Galectin3binding protein | 46 | 134 | 2 |
| 16 | IPI00385896.1 | SPP1 | Isoform D of Osteopontin | 27 | 109 | 2 |
| 17 | IPI00293088.4 | GAA | 106 kDa protein | 28 | 114 | 2 |
| 18 | IPI00008787.3 | NAGLU | AlphaNacetylglucosaminidase | 27 | 96 | 2 |
| 19 | IPI00741768.1 | LOC64213 | PREDICTED: similar to Maltaseglucoamylase, intestinal | 25 | 114 | 2 |
| 20 | IPI00003919.1 | QPCT | Glutaminylpeptide cyclotransferase | 30 | 87 | 2 |
| 21 | IPI00783792.1 | MGAM | 192 kDa protein | 10 | 43 | 2 |
| 22 | IPI00220143.2 | MGAM | Maltaseglucoamylase, intestinal | 22 | 97 | 2 |
| 23 | IPI00240345.3 | CLEC14A | Ctype lectin domain family 14 member A | 5 | 29 | 3 |

We performed non-invasive, peptidomic analysis using mass spectrometry, followed by MRM verification and analyzed 70 urine samples from unique renal transplant patients (n=50) and controls (n=20). We identified a specific panel of 53 peptides for acute rejection (AR). Peptide sequencing revealed underlying mechanisms of graft injury with a pivotal role for proteolytic degradation of uromodulin (UMOD) and a number of collagens (Table 5A). Integrative analysis of transcriptional signals from paired renal transplant biopsies, matched with the urine samples, reveal coordinated transcriptional changes for the corresponding genes, in addition to dysregulation of extra-cellular matrix proteins in AR (MMP7, SERPING1 and TIMP1). Q-PCR on an independent set of 34 transplant biopsies, with and without AR, validates coordinated changes in expression for the corresponding genes in rejection tissue, with a 6 gene biomarker panel (COL1A2, COL3A1, UMOD, MMP7, SERPING1, TIMP1) that can also classify AR with high specificity and sensitivity (ROC, AUC 0.98) (Table 5b).

TABLE 5A

| Protein Precursor | PeptideMass (Da) | Peptide Seq |
|---|---|---|
| Collagen alpha alpha-1(XVIII) | 1142.53 | GPPGPPGPPGPPS |
| Collagen alpha 3(IV) | 1161.51 | GEPGPPGPPGNLG |
| Collagen alpha-4(IV) | 1219.55 | GLPGPPGPKGPRG |
| Collagen alpha-4(IV) | 1220.55 | GLPGPPGPKGPRG |
| Collagen alpha-4(IV) | 1221.56 | GLPGPPGPKGPRG |
| Collagen alpha-1(I) | 1251.55 | APGDRGEPGPPGP |
| Collagen alpha-1(I) | 1251.55 | APGDRGEPGPPGP |
| Collagen alpha-1(I) | 1409.65 | GPPGPPGPPGPPGPPS |
| Collagen alpha-1(VII) | 1692.81 | PGLPGQVGETGKPGAPGR |
| Collagen alpha-5(IV) | 1733.77 | GIKGEKGNPGQPGLPGLP |
| Collagen alpha-1(I) | 2064.92 | NGDDGEAGKPGRPGERGPPGP |
| Collagen alpha-1(I) | 2066.92 | NGDDGEAGKPGRPGERGPPGP |
| Collagen alpha-2(I) | 2081.93 | DGPPGRDGQPGHKGERGYPG |
| Collagen alpha-1(I) | 3014.44 | ESGREGAPGAEGSPGRDGSPGAKGDRGETGPA |
| Uromodulin | 1681.98 | VIDQSRVLNLGPITR |
| Uromodulin | 1912.07 | SGSVIDQSRVLNLGPITR |

TABLE 5B

| Gene Symbol | AR | STA | P-Value | Fold Change | Increase/Decrease |
| --- | --- | --- | --- | --- | --- |
| COL1A2 | 8.55 | 2.27 | 0.03 | 3.8 | Increase |
| COL3A1 | 13.53 | 2.93 | 0.02 | 4.6 | Increase |
| MMP7 | 10.85 | 0.79 | 0.01 | 13.8 | Increase |
| SERPING1 | 6.48 | 0.91 | 0.00 | 7.1 | Increase |
| TIMP1 | 15.80 | 1.27 | 0.01 | 12.5 | Increase |
| UMOD | 0.46 | 1.17 | 0.08 | 2.5 | Decrease |

The unique approach of integrated urine peptidomic and biopsy transcriptional analyses reveal that key collagen remodeling pathways are modulated in AR tissue, and may be the trigger for downstream chronic graft fibrosis after an AR episode. The proteolytic degradation products of the corresponding proteins in urine provide a unique non-invasive tool for diagnosis of AR.

Aspects of the subject invention include methods of determining the clinical transplant category of a subject who has received a kidney transplant. Clinical transplant categories include, but are not limited to: acute rejection (AR) response, stable allograft (STA), nephrotic syndrome (NS) and the like.

Listed above are gene and protein biomarkers for transplant injury. We have also applied customized informatics algorithms to identify antibody based biomarkers for any kind of injury to the kidney, in this case even focusing on the native kidney.

We used high-density protein arrays to analyze 60 serum samples collected from 20 renal patients at 0, 6, and 24 months post-transplant matching with protocol biopsies. Protein arrays with approximately 8300 antigens were used and the data was analyzed to identify CAI specific antibodies and their correlation with chronic injury progression. A repertoire of 111 nHLA antibodies significantly increased in response to chronic allograft injury of which 31 antibodies track allograft injury. Antibody level of a set of 5 antibodies (CXCL9/MIG, CXCL11/ITAC, IFN-Gamma, CCL21/6CK-INE, and GDNF) at the time of implantation was found to be correlated with injury progression.

TABLE 6

CAI specific Abs correlate with CADI score and IFTA scores:

| S. No. | Gene Symbol | CADI, r, p | IF-TA r, p |
| --- | --- | --- | --- |
| 1 | IFNG | 0.68, <0.0001 | 0.61, <0.0001 |
| 2 | CXCL9/MIG | 0.61, <0.0001 | 0.55, 0.0002 |
| 3 | CXCL11/ITAC | 0.51, 0.0009 | 0.42, 0.0072 |
| 4 | CSNK2A2 | 0.51, 0.0008 | 0.52, 0.0006 |
| 5 | GDNF | 0.63, <0.0001 | 0.58, <0.0001 |
| 6 | BHMT2 | 0.47, 0.002 | 0.54, 0.0003 |
| 7 | 6CKINE | 0.56, 0.0002 | 0.54, 0.0003 |
| 8 | CSNK2A1 | 0.50, 0.0011 | 0.54, 0.0004 |
| 9 | J0-1(HARS) | 0.63, <0.0001 | 0.63, <0.0001 |
| 10 | CSNK1G1 | 0.49, 0.0012 | 0.51, 0.0008 |
| 11 | IL21 | 0.57, 0.0001 | 0.51, 0.0008 |
| 12 | CSNK1G3 | 0.35, 0.0263 | 0.43, 0.006 |
| 13 | IL-8 | 0.43, 0.006 | 0.48, 0.002 |
| 14 | PRKCE | 0.41, 0.009 | 0.48, 0.002 |
| 15 | FLJ21908 | 0.48, 0.002 | 0.47, 0.002 |
| 16 | WIBG | 0.39, 0.01 | 0.46, 0.003 |
| 17 | ATXN3 | 0.46, 0.003 | 0.45, 0.003 |
| 18 | RNAPOL | 0.39, 0.01 | 0.45, 0.004 |
| 19 | MAPRE2 | 0.34, 0.03 | 0.45, 0.004 |
| 20 | CCL19 | 0.40, 0.009 | 0.43, 0.006 |

We performed ELISA assay to validate findings based on protein arrays. A set of antibodies based on their statistical significance and biological relevance was selected for validation by ELISA assay. We performed ELISA measurement of antibodies and demonstrated their validity in separating CAI from NCAI groups as well as the predictive ability of two of the antibodies level at 6 month to injury progression at 24 mo. Elisa assays were developed and optimized to validate discovery made by protein array platform. We performed ELISA assays on 4 antigens (MIG/CXCL9, ITAC/CXCL11, CSNK2A2, and PDGFRA) to validate the observation made by the protein array platform. Serum collected from renal transplant patients with biopsy proven nCAI (n=30) and serum collected from renal transplant patients with biopsy proven CAI (n=31) were included. A significant increase of CXCL9/MIG ($p<0.02$), CXCL11/ITAC ($p<0.014$), CSNK2A2 ($p<0.0002$), and PDGFRA ($p<0.0001$) was observed for CAI group compared to nCAI.

In certain embodiments the method includes: (a) evaluating the amount of one or more peptides/proteins in a urine sample from a transplant subject to obtain a protein signature; and (b) determining the transplant category of the subject based on the protein signature. In certain embodiments, the protein signature comprises protein level data for one or more proteins in any of Tables 4A to 4C and 5A.

As summarized above, aspects of the subject invention provide methods for determining a clinical transplant category of a subject who has received a kidney transplant, as well as reagents, systems, kits and computer program products for use in practicing the subject methods. In further describing the invention, the subject methods are described first, followed by a review of the reagents, systems, kits and computer program products for use in practicing the subject methods.

Methods for Determining a Clinical Transplant Category

Aspects of the subject invention include methods for determining a clinical transplant category of a subject who has received a kidney transplant.

As is known in the transplantation field, a graft organ, tissue or cell(s) may be allogeneic or xenogeneic, such that the grafts may be allografts (solid organ and bone marrow) or xenografts.

In certain embodiments, the method can be considered a method of monitoring a subject to determine a clinical transplant category, e.g., at one or more time points after kidney transplantation. Clinical transplant categories that can be determine using the methods of the subject invention include, but are not limited to: acute allograft rejection (AR) and stable allograft (STA). In certain embodiments, the subject methods distinguish one or more of the clinical transplant categories from non-transplant categories, including subjects with non-specific proteinuria with native renal diseases (nephrotic syndrome, or NS), subjects with healthy kidney function (HC), subjects with chronic or acute graft vs. host disease (GVHD), etc.

In practicing the subject methods, the urine sample is assayed to obtain a protein signature of the sample, or protein profile, in which the amount of one or more specific peptides/proteins in the sample is determined, where the determined amount may be relative and/or quantitative in nature. In certain embodiments, the protein signature includes measurements for the amount of one or more proteins (or peptides derived therefrom) shown in Tables 4A to 4C and 5A.

As detailed in the Examples section below, tissue, blood or urine gene expression or urine protein analysis identified different gene and/or protein signatures with predictive power for clinical transplant categories. The term gene profile is used to denote determining the expression, at the mRNA level, one or more genes in a sample; protein profile is used broadly to include a profile of one or more different proteins/peptides in the sample, where the proteins are derived from expression products of one or more genes. As such, in certain embodiments, the level of expression only one gene and/or protein shown in any of Tables is evaluated. In yet other embodiments, the expression level of two or more genes and or proteins from any of Tables is evaluated, e.g., 3 or more, 5 or more, 10 or more, 20 or more, 100 or more, etc. It is noted that the expression level of one or more additional genes and/or proteins other than those listed in Tables can also be evaluated in the gene and/or protein signature.

The gene/protein/peptide signature of a sample can be obtained using any convenient method for gene expression/protein/peptide analysis. As such, no limitation in this regard is intended. Exemplary peptide analysis includes, but is not limited to: HPLC, mass spectrometry, LC-MS based peptide profiling (e.g., LC-MALDI), Multiple Reaction Monitoring (MRM), ELISA, microarray, QPCR and the like. In the broadest sense, gene and or protein expression evaluation may be qualitative or quantitative. As such, where detection is qualitative, the methods provide a reading or evaluation, e.g., assessment, of whether or not the target analyte (e.g., gene or protein) is present in the sample being assayed. In yet other embodiments, the methods provide a quantitative detection of whether the target analyte is present in the sample being assayed, i.e., an evaluation or assessment of the actual amount or relative abundance of the target analyte, e.g., gene and/or protein in the sample being assayed. In such embodiments, the quantitative detection may be absolute or, if the method is a method of detecting two or more different analytes in a sample, relative. As such, the term "quantifying" when used in the context of quantifying a target analyte in a sample can refer to absolute or to relative quantification. Absolute quantification may be accomplished by inclusion of known concentration(s) of one or more control analytes and referencing the detected level of the target analyte(s) with the known control analytes (e.g., through generation of a standard curve). Alternatively, relative quantification can be accomplished by comparison of detected levels or amounts between two or more different target analytes to provide a relative quantification of each of the two or more different analytes, e.g., relative to each other. In addition, a relative quantitation may be ascertained using a control, or reference, value (or profile) from one or more control sample. Control/reference profiles are described in more detail below.

In certain embodiments, additional analytes beyond those listed above may be assayed, where the additional analytes may be additional proteins, additional nucleic acids, or other analytes. For example, genes whose expression level/pattern is modulated under different transplant conditions (e.g., during an AR response) can be evaluated (e.g., from a biopsy sample, blood sample, urine sample, etc. from the subject). In certain embodiments, additional analytes may be used to evaluate additional transplant characteristics, including but not limited to: a graft tolerant phenotype in a subject, chronic allograft injury (chronic rejection); immunosuppressive drug toxicity, GVHD, or adverse side effects including drug-induced hypertension; age or body mass index associated genes that correlate with renal pathology or account for differences in recipient age-related graft acceptance; immune tolerance markers; genes found in literature surveys with immune modulatory roles that may play a role in transplant outcomes. In addition, other function-related genes may be evaluated, e.g., for assessing sample quality (3'- to 5'-bias in probe location), sampling error in biopsy-based studies, cell surface markers, and normalizing proteins/genes for calibrating results.

In practicing the methods of the present invention, any convenient gene and/or protein evaluation/quantitation protocol may be employed, where the levels of one or more genes/proteins in the assayed sample are determined to generate a gene and/or protein signature for the sample. Representative methods include, but are not limited to: MRM analysis, standard immunoassays (e.g., ELISA assays, Western blots, FACS based protein analysis, etc.), protein activity assays, including multiplex protein activity assays, QPCR, expression arrays, etc. Following obtainment of the gene and/or protein signature from a subject, the gene/protein signature is analyzed/evaluated to determine a transplant category of the subject (e.g., whether the subject is undergoing an AR response). In certain embodiments, analysis includes comparing the protein signature with a reference or control signature, e.g., a reference or control; gene/protein signature, to determine the transplant category of the transplant subject. The terms "reference" and "control" as used herein mean a standardized analyte level (or pattern) that can be used to interpret the analyte pattern of a sample from a subject. For example, a reference profile can include gene/protein level data for one or more gene/protein of interest being evaluated in the sample of the subject/patient. The reference or control profile may be a profile that is obtained from a subject (a control subject) having an AR phenotype, and therefore may be a positive reference or control signature for AR. In addition, the reference/control profile may be from a control subject known to not be undergoing AR (e.g., STA, NS or HC), and therefore be a negative reference/control signature.

In certain embodiments, the obtained gene/protein signature is compared to a single reference/control profile to determine the subject's transplant category. In yet other embodiments, the obtained gene/protein signature is compared to two or more different reference/control profiles to obtain additional or more in depth information regarding the transplant category of the subject. For example, the obtained gene/protein signature may be compared to a positive and negative reference profile to obtain confirmed information regarding whether the subject is undergoing an AR response.

The comparison of the obtained gene/protein signature and the one or more reference/control profiles may be performed using any convenient methodology, where a variety of methodologies are known to those of skill in the array art, e.g., by comparing digital images of the gene/protein signatures by comparing databases of peptide signatures and/or gene expression profiles, etc. Patents describing ways of comparing expression profiles include, but are not limited to, U.S. Pat. Nos. 6,308,170 and 6,228,575, the disclosures of which are herein incorporated by reference.

The comparison step results in information regarding how similar or dissimilar the obtained gene/protein signature is to the control/reference profile(s), which similarity/dissimilarity information is employed to determine the transplant category of the subject. For example, similarity of the obtained gene/protein signature with the gene/protein signature of a control sample from a subject experiencing an active AR response indicates that the subject is experiencing AR. Likewise, similarity of the obtained gene/protein signature with the protein signature of a control sample from a subject that has not had (or isn't having) an AR episode (e.g., STA) indicates that the subject is not experiencing AR.

Depending on the type and nature of the reference/control profile(s) to which the obtained gene/protein signature is compared, the above comparison step yields a variety of different types of information regarding the subject as well as the sample employed for the assay. As such, the above comparison step can yield a positive/negative determination of an ongoing AR response. In certain embodiments, the determination/prediction of AR can be coupled with a determination of additional characteristics of the graft and function thereof. For example, in certain embodiments one can assay for other graft-related pathologies, e.g., chronic rejection (or CAN) and/or drug toxicity (DT), graft vs host disease (GVHD), BKVN (see, e.g., U.S. patent application Ser. No. 11/375,681, filed on Mar. 3, 2006, which is incorporated by reference herein in its entirety).

In certain embodiments, a reference profile is a composite reference profile, having control data derived from more than one subject and/or sample. For example, a reference profile may include average protein level data from urine samples from subjects having the same or similar transplant categories.

The subject methods further find use in pharmacogenomic applications. In these applications, a subject/host/patient is first monitored for their clinical transplant category (e.g., for an AR response) according to the subject invention, and then treated using a protocol determined, at least in part, on the results of the monitoring. For example, a host may be evaluated for the presence or absence of AR using a protocol such as the diagnostic protocol described above. The subject may then be treated using a protocol whose suitability is determined using the results of the monitoring step. For example, where the subject is categorized as having an AR response, immunosuppressive therapy can be modulated, e.g., increased or drugs changed, as is known in the art for the treatment/prevention of AR. Likewise, where the subject is categorized as free of AR, the immunosuppressive therapy can be reduced, e.g., in order to reduce the potential for DT.

In practicing the subject methods, a subject is typically monitored for AR following receipt of a graft or transplant. The subject may be screened once or serially following transplant receipt, e.g., weekly, monthly, bimonthly, half-yearly, yearly, etc. In certain embodiments, the subject is monitored prior to the occurrence of an AR episode. In certain other embodiments, the subject is monitored following the occurrence of an AR episode.

The subject methods may be employed with a variety of different types of transplant subjects. In many embodiments, the subjects are within the class mammalian, including the orders carnivore (e.g., dogs and cats), rodentia (e.g., mice, guinea pigs, and rats), lagomorpha (e.g. rabbits) and primates (e.g., humans, chimpanzees, and monkeys). In certain embodiments, the animals or hosts, i.e., subjects (also referred to herein as patients) are humans.

Aspects of the present invention include methods of determining whether a subject who has received a kidney or other solid organ allograft is undergoing an acute rejection (AR) response by evaluating the level of one or more genes and/or proteins in a blood and/or urine sample from the subject to obtain a gene/protein signature and determining whether the subject is undergoing an AR response based on the gene/protein signature. In certain embodiments, the one or more genes/proteins includes at least one gene/protein selected from the Tables. In addition, the present invention also provides a method for determining whether a subject who has received a bone marrow transplant is undergoing chronic graft vs host disease (GVHD). As such, the gene/protein signature may contain include gene/protein level expression date for one gene/protein, 2 or more genes/proteins, 3 or more genes/proteins, 5 or more genes/proteins, 10 or more genes/proteins, 20 or more genes/proteins, etc. that are listed in any of Tables. The selection of which gene or genes, protein or proteins from the Tables are to be included in the gene/protein signature will be determined by the desires of the user. Thus, the gene/protein signature may contain protein level expression data for at least one gene/protein from a single table, from two tables, three tables, or from all of Tables. No limitation in this regard is intended.

In certain embodiments, the one or more gene/protein in the gene and/or protein signature includes the protein CD44, UMOD and PEDF in the urine. In such embodiments, the subject is determined to be undergoing an AR response when either single and/or combined levels of CD44, UMOD and PEDF protein in the urine sample is decreased as compared a non-AR control reference protein signature. In certain embodiments, the one or more protein includes a protein selected from a Table, where the subject is determined to be undergoing an AR response when the protein selected from a Table is detected in the gene/protein signature. Any number of gene/proteins listed in Tables may be evaluated, including 1 or more, 3 or more, 5 or more, and including all of the genes/proteins listed in in the Tables. Any number of genes/proteins listed in Tables may be evaluated, including 1 or more, 3 or more, 5 or more, and including all of the genes/proteins listed in the Tables. The subject is determined to be undergoing an AR response or BKVN response or CAI response, when the level of the protein and/or genes selected from any of the Tables is either statistically increased or decreased in the gene/protein signature as compared to a non-injury or a stable (STA) control reference protein and/or gene signature.

Addition signatures for proteins found only in the urine of healthy controls (HC), proteins found only in the urine of NS controls, and proteins found only in the urine subjects not undergoing AR are listed in Tables 3, 5, and 7 respectively, of U.S. Provisional Application Ser. No. 61/341,071 (to which this application claims priority). As such, in certain embodiments, any one or more of these proteins may be evaluated to determine a transplant category for a subject as described herein. For example, one or more proteins in Tables 3, 5 and/or 7 of U.S. Provisional Application Ser. No. 61/341,071 may be included in a reference or control profile for determining a transplant category (e.g., as a negative control for an AR response). As another example, one or more of the proteins listed in these tables can be evaluated where their detection indicates that a urine sample is derived from a healthy subject (Table 3), a NS subject (Table 5), or a subject not undergoing an AR response (Table 7).

Combinations

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to proteins that find use as markers for monitoring a renal transplant (e.g., determining the status of a renal graft, e.g., AR, NS, STA, etc.) or any other solid organ or bone marrow transplant are specifically embraced by the present invention and are disclosed herein just as if each and every combination was individually and explicitly disclosed. As such, any combination of genes/proteins from one or more of any of the tables described herein are disclosed herein just as if each and every such sub-combination of proteins was individually and explicitly disclosed herein.

Databases of Expression Profiles of Phenotype Determinative Genes

Also provided are databases of gene expression/protein signatures of different transplant categories, e.g., AR, STA, NS and the like. The gene expression/protein signatures and databases thereof may be provided in a variety of media to facilitate their use (e.g., in a user-accessible/readable format). "Media" refers to a manufacture that contains the expression profile information of the present invention. The databases of the present invention can be recorded on computer readable media, e.g. any medium that can be read and accessed directly by a user employing a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising a recording of the present database information. "Recorded" refers to a process for storing information on computer readable medium, using any such methods as known in the art. Any convenient data storage structure may be chosen, based on the means used to access the stored information. A variety of data processor programs and formats can be used for storage, e.g. word processing text file, database format, etc. Thus, the subject expression profile databases are accessible by a user, i.e., the database files are saved in a user-readable format (e.g., a computer readable format, where a user controls the computer).

As used herein, "a computer-based system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

A variety of structural formats for the input and output means can be used to input and output the information in the computer-based systems of the present invention, e.g., to and from a user. One format for an output means ranks expression profiles (e.g., a gene expression/protein signature) possessing varying degrees of similarity to a reference expression profile (e.g., a reference gene expression/protein signature). Such presentation provides a skilled artisan (or user) with a ranking of similarities and identifies the degree of similarity contained in the test expression profile to one or more references profile(s).

As such, the subject invention further includes a computer program product for determining a clinical transplant category of a subject who has received a kidney allograft. The computer program product, when loaded onto a computer, is configured to employ a gene expression/protein signature from a urine sample from a subject to determine a clinical transplant category for the subject. Once determined, the clinical transplant category is provided to a user in a user-readable format. In certain embodiments, the gene expression/protein signature includes data for the gene expression/protein level of one or more peptides listed in Tables 3 to 10 (or any combination thereof as described herein). In addition, the computer program product may include one or more reference or control gene expression/protein signatures (as described in detail above) which are employed to determine the clinical transplant category of the patient.

Thus, aspects of the present invention include computer program products for determining whether a subject who has received a kidney allograft is undergoing an AR response. The computer program product, when loaded onto a computer, is configured to employ a gene expression/protein signature from a urine sample from the subject to determine whether the subject is undergoing an AR response, and provide the determined AR response to a user in a user-readable format, wherein the gene expression/protein signature comprises data for the protein and/or gene level of one or more of the proteins/genes listed in any of the Tables.

Reagents, Systems and Kits

Also provided are reagents, systems and kits thereof for practicing one or more of the above-described methods. The subject reagents, systems and kits thereof may vary greatly. Reagents of interest include reagents specifically designed for use in production of the above-described gene expression/protein signatures. These include a gene expression/protein level evaluation element made up of one or more reagents. The term system refers to a collection of reagents, however compiled, e.g., by purchasing the collection of reagents from the same or different sources. The term kit refers to a collection of reagents provided, e.g., sold, together.

The subject systems and kits include reagents for peptide/protein or gene expression (e.g., mRNA) level determination, for example those that find use in ELISA assays, Western blot assays, MS assays (e.g., LC-MS), HPLC assays, flow cytometry assays, array based assays, PCR, hybridization assays, Northern blots, and the like. One type of such reagent is one or more probe specific for one or more proteins listed any of the tables described herein.

For example, antibody or binding fragments thereof (as are well known in the art) find us in the subject systems as probes for peptides/proteins. In certain embodiments, antibody arrays containing antibodies at known locations on a substrate are provided in the subject systems (see, e.g., U.S. Pat. Nos. 4,591,570; 5,143,854; 7,354,721; the disclosures of which are herein incorporated by reference). Probes for any combination of genes listed in the tables described herein may be employed. The subject arrays may include probes for only those proteins that are listed in tables described herein or they may include additional proteins that are not listed therein, such as probes for proteins whose expression pattern can be used to evaluate additional transplant characteristics as well as other array assay function related proteins, e.g., for assessing sample quality, sampling error, and normalizing protein levels for calibrating results, and the like.

As another example, gene expression may be evaluated using a reagent that includes gene-specific probes. One type of such reagent is an array of probe nucleic acids in which the phenotype determinative genes of interest are represented. A variety of different array formats are known in the art, with a wide variety of different probe structures, substrate compositions and attachment technologies. In many embodiments, the arrays include probes for 1 or more of the genes listed in the tables described herein. The subject arrays may include only those genes that are listed in the tables, or they may include additional genes that are not listed (e.g., as controls or for determination of other phenotypes of the subject or condition of the sample). Another type of reagent that is specifically tailored for generating expression profiles of phenotype determinative genes is a collection of gene specific primers that is designed to selectively amplify such genes.

The systems and kits of the subject invention may include the above-described arrays and/or specific probes or probe collections. The systems and kits may further include one or more additional reagents employed in the various methods, such as various buffer mediums, e.g. hybridization and washing buffers, prefabricated probe arrays, labeled probe purification reagents and components, like spin columns, etc., signal generation and detection reagents, e.g. secondary antibodies (e.g., conjugated to detectable moieties, e.g., horseradish peroxidase (HRP), alkaline phosphatase, etc.), chemifluorescent or chemiluminescent substrates, fluorescent moieties, and the like.

The subject systems and kits may also include a phenotype determination element, which element is, in many embodiments, a reference or control peptide signature or gene expression profile that can be employed, e.g., by a suitable computing means, to determine a transplant category based on an "input" protein signature. Representative phenotype determination elements include databases of protein signatures, e.g., reference or control profiles, as described above.

In addition to the above components, the subject systems/ kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

Aspects of the present invention thus provide systems for determining whether a subject who has received a kidney allograft is undergoing an acute rejection (AR) response. The system includes: a protein level evaluation element configured for evaluating the level of one or more protein in a urine sample from a subject who has received a kidney allograft to obtain a protein signature, where the one or more protein includes a protein selected from: Table 4A to 4C and/or 5A; and a phenotype determination element configured for employing the protein signature to determine whether the subject is undergoing an AR response.

In certain embodiments, the one or more protein in the protein signature includes the protein CD44. In certain embodiments, the one or more protein further includes UMOD and PEDF.

In certain embodiments, the one or more protein includes a protein selected from Table 4A. Any number of proteins listed in Table 4A may be evaluated, including 1 or more, 3 or more, 5 or more, and including all of the proteins listed in Table 4A.

In certain embodiments, the one or more protein includes a protein selected from Table 4B. Any number of proteins listed in Table 4B may be evaluated, including 1 or more, 3 or more, 5 or more, and including all of the proteins listed in Table 4B.

In certain embodiments, the one or more protein includes a protein selected from Table 4C. Any number of proteins listed in Table 4C may be evaluated, including 1 or more, 3 or more, 5 or more, and including all of the proteins listed in Table 4C.

In certain embodiments, the one or more protein includes a protein selected from Table 5A. Any number of proteins listed in Table 5A may be evaluated, including 1 or more, 3 or more, 5 or more, and including all of the proteins listed in Table 5A.

As noted, U.S. Provisional Application Ser. No. 61/341, 071 (to which this application claims priority) describes proteins found only in the urine of healthy controls (HC) (Table 3 of U.S. Provisional Application Ser. No. 61/341, 071), proteins found only in the urine of NS controls are listed in (Table 5 of U.S. Provisional Application Ser. No. 61/341,071), and proteins found only in the urine subjects not undergoing AR are listed in (Table 7 of U.S. Provisional Application Ser. No. 61/341,071). As such, in certain embodiments, systems/kits of the invention may include a protein level evaluation element for any one or more of these proteins.

The following examples are offered by way of illustration and not by way of limitation.

EXPERIMENTAL

Introduction

Acute rejection (AR) remains the primary risk factor for renal transplant outcome; development of non-invasive diagnostic biomarkers for AR is an unmet need. We used shotgun proteomics using LC-MS/MS and ELISA to analyze a set of 92 urine samples, from patients with AR, stable grafts (STA), proteinuria (NS), and healthy controls (HC). A total of 1446 urinary proteins were identified along with a number of NS specific, renal transplantation specific and AR specific proteins. Relative abundance of identified urinary proteins was measured by protein-level spectral counts adopting a weighted fold-change statistic, assigning increased weight for more frequently observed proteins. We have identified alterations in a number of specific urinary proteins in AR, primarily relating to MHC antigens, the complement cascade and extra-cellular matrix proteins. A subset of proteins (UMOD, SERPINF1 and CD44), have been further cross-validated by ELISA in an independent set of urine samples, for significant differences in the abundance of these urinary proteins in AR. This label-free, semi-quantitative approach for sampling the urinary proteome in normal and disease states provides a robust and sensitive method for detection of urinary proteins for serial, non-invasive clinical monitoring for graft rejection after kidney transplantation.

We have undertaken a pilot study of 10 normal samples, 40 urinary samples from patients with nephrotic syndrome as well as renal transplant patients with stable graft function and biopsy proven AR. The purpose of the study was to determine if phenotype specific differences could be identified in urinary samples from patients with different etiologies of native and transplant-associated renal injury.

The benefit of identifying rejection specific urinary proteomic biomarkers in urine is very relevant. Renal transplantation is the ultimate treatment for patients with end stage kidney disease 14, but there is no current non-invasive means to monitor for acute graft rejection. Renal biopsy is an invasive procedure that suffers from sampling heterogeneity, has associated complications of pain, sedation, hematuria, arteriovenous fistulae, graft thrombosis and transfusion risk, and correlates poorly with treatment response and prognosis. Because of the ability of urine to reflect both local processes within the kidney as well as a reflection of changes within plasma, urine is particularly useful to diagnose kidney diseases and kidney transplant dysfunction (Clin Chim Acta 2007, 375, (1-2), 49-56). Discovery of a urine biomarker for assessing the rejection status of patients following kidney transplant could significantly improve patient outcomes and decrease cost of care.

To test the validity of the proteomic discovery for AR specific biomarkers by our study approach, we performed ELISA assays on selected protein biomarkers using an independent set of 52 unique patient urines. ELISA results established that the approach taken in this study is a viable way to discover potential biomarkers. This report demonstrates how high-throughput, high-cost, labor-intensive MS-based discovery can eventually be developed into an economical, rapid turn-around, clinically applicable diagnostic assay for transplant patients.

Materials and Methods

Materials:

The following reagents were used for the proteomics sample preparation: nanopure or Milli-Q quality water (~18 megohm·cm or better); Bicinchoninic acid (BCA) Assay Kit was purchased from Pierce (Rockford, Ill.); Amicon Ultra centrifugal filtration tubes were obtained from Millipore (Bedford, Mass.) ammonium bicarbonate, ammonium formate, and formic acid were obtained from Fluka (St. Louis, Mo.); Tris.HCl, urea, thiourea, dithiothreitol (DTT), iodoacetamide, calcium chloride, and trifluoroacetic acid (TFA), were obtained from Sigma-Aldrich (St. Louis, Mo.); HPLC-grade methanol (MeOH) and HPLC-grade acetonitrile ($CH_3CN$) were purchased from Fisher Scientific (Fair Lawn, N.J.); 2,2,2-trifluoroethanol (TFE) was obtained from Aldrich Chemical Company, Inc. (Milwaukee, Wis.); and sequencing grade modified trypsin was purchased from Promega (Madison, Wis.). PEDF ELISA kit was purchased from Bioproducts MD (Middletown, Md.).

Samples:

Forty individual and clinically annotated urine samples were included in the study. We used 10 renal transplant patients, each with biopsy proven acute rejection (AR) and 10 renal transplant patients with biopsy proven stable grafts (STA). Our controls included 10 non-specific proteinuria (NS) patients and 10 age matching healthy children as healthy controls (HC). Patient demographics were matched. The samples were collected in between January 2005 and June 2007 and were obtained as part of an ongoing IRB approved study at Stanford University. Approval for the conduct of this research was obtained from the Institutional Review boards at Stanford University and Pacific Northwest National Laboratory (PNNL) in accordance with federal regulations.

Urine Collection, Initial Processing and Storage:

Second morning void mid-stream urine samples (50-100 mL) were collected in sterile containers and were centrifuged at 2000×g for 20 min at room temperature within 1 h of collection. The supernatant was separated from the pellet containing any particulate matter including cells and cell debris. The pH of the supernatant was adjusted to 7.0 and stored at −80° C. until further analysis.

Recovering and Quantification of Urinary Protein:

Urinary proteins were isolated by removing small MW peptides and other pigments (<10 kDa) by filtering the supernatant through Amicon Ultra centrifugal filtration tubes (Millipore, Bedford, Mass.). The tubes were pre-equilibrated with 10 mL Milli-Q water and centrifuging at 3000×g for 10 min at 10° C. using swinging bucket rotors. After equilibration, 10 mL of urine supernatant was centrifuged for 20 min at 3000×g at 10° C. The filtrate was recovered and saved for peptidomic analysis. The retentate was washed twice with 10 mL of 20 mM Tris-HCl (pH 7.5). The final volume of the retentate was brought to 400 µL with 20 mM Tris-HCl (pH 7.5) and was quantified by using bicinchoninic acid (BCA) protein assay (Pierce, Rockford, Ill.). After the quantification of individual samples, 4 pooled samples for each AR (acute rejection), STA (stable), NS (non-specific proteinuria; nephrotic syndrome) and HC (healthy control) categories were prepared using 200 µg from each individual samples in each category.

Urinary Proteomic Sample Preparation:

Samples were desalted using Micron Ultracel YM-3 centrifugal filters MWCO 3000 (Millipore, Billerica, Mass.) prior to the tryptic digestion following the manufacturer's protocol. Protein concentration was verified after buffer exchange using a BCA Protein Assay. A mixture of 3 standard proteins, purchased individually from Sigma-Aldrich (horse apomyoglobin, rabbit glyceraldehyde-3-phosphate dehydrogenase, and bovine ovalbumin), was added for quality control purposes. Proteins were denatured in 50 mM ammonium bicarbonate, pH 7.8, 8 M Urea for 1 h at 37° C. and then reduced with 10 mM DTT at 37° C. for 1 h. After this they were alkylated with 40 mM iodoacetamide at room temperature for 1 h in the absence of light. Samples were diluted 10 fold with 50 mM ammonium bicarbonate, pH 7.8 and sufficient amount of 1 M calcium chloride was added to the samples to obtain a concentration of 1 mM in the sample. Sequencing grade-modified trypsin was prepared by adding 20 µL of 50 mM ammonium bicarbonate, pH 7.8 to a vial containing 20 µg trypsin and after 10 min incubation at 37° C. was used for digestion of the samples. Tryptic digestion was performed for 3 h at 37° C. with 1:50 (w/w) trypsin-to-protein ratio. Rapid freezing of the samples in liquid nitrogen quenched the enzymatic digestion.

Digested samples were desalted by using a solid-phase extraction (SPE) C18 column (Discovery DSC-18, SUPELCO, Bellefonte, Pa.) conditioned with MeOH and rinsed with 0.1% TFA, 1 mL, and washed with 4 mL of 0.1% TFA/5% $CH_3CN$. Peptides were eluted from the SPE column with 1 mL of 0.1% TFA/80% $CH_3CN$ and concentrated in Speed-Vac SC 250 Express (Thermo Savant, Holbrook, N.Y.) to a volume of ~50-100 µL. The peptide concentration was measured using the BCA Protein Assay. Digested samples were stored at −80° C. until needed for analysis or further processing.

Strong Cation Exchange (SCX) Fractionation:

Digested samples (200.0-350.0 µg) were reconstituted with 900 µL of 10 mM ammonium formate, pH 3.0/25% $CH_3CN$ and fractionated by SCX chromatography on a Polysulfoethyl A 2.1 mm×200 mm, 5 µM, 300 Å column with 2.1 mm×10 mm guard column (PolyLC, Inc., Columbia, Md.) using an Agilent 1100 series HPLC system (Agilent, Palo Alto, Calif.). The flow rate was 200 µL/min, and mobile phases were 10 mM ammonium formate, pH 3.0/25% $CH_3CN$ (A), and 500 mM ammonium formate, pH 6.8/25% $CH_3CN$ (B). After loading 900 µL of sample onto the column, the mobile phase was maintained at 100% A for 10 min. Peptides were then separated using a gradient from 0 to 50% B over 40 min, followed by a gradient of 50-100% B the following 10 min. The mobile phase was held at 100% B for 10 min, followed by $H_2O$ rinsing for the next 20 min and final re-conditioning with A for 10 min. A total of 60 fractions over 90 min separation were collected for each depleted sample, and each fraction was dried under vacuum in Speed-Vac. The fractions were dissolved in 25 µL of 25 mM ammonium bicarbonate, pH 7.8 and combined into 32 fractions for LC-MS/MS analysis. The first 20 fractions were combined into one and were desalted by C18 SPE column (Discovery DSC-18, SUPELCO, Bellefonte, Pa.), the next 30 fractions were not pooled and each was analyzed separately, and 5.0 µL of each of the last 10 fractions were combined together into fraction number 32. A 5.0 µL aliquot of each fraction was analyzed by capillary LC-MS/MS.

Capillary LC-MS/MS Analysis:

The HPLC system consisted of a custom configuration of 100-mL Isco Model 100DM syringe pumps (Isco, Inc., Lincoln, Nebr.), 2-position Valco valves (Valco Instruments Co., Houston, Tex.), and a PAL autosampler (Leap Technologies, Carrboro, N.C.), allowing for fully automated sample analysis across four separate HPLC columns (Anal Chem 2008, 80, (1), 294-302). Reversed phase capillary HPLC columns were manufactured in-house by slurry packing 3-µm Jupiter C18 stationary phase (Phenomenex, Torrence, Calif.) into a 60-cm length of 360 µm o.d.×75 µm i.d. fused silica capillary tubing (Polymicro Technologies Inc., Phoenix, Ariz.) that incorporated a 2.0-µm retaining screen in a ¹⁄₁₆" 75 µm i.d. union (Valco Instruments Co., Houston, Tex.). Mobile phase consisted of 0.2% acetic acid and 0.05% TFA in water (A) and 0.1% TFA in 90% $CH_3CN$/10% water (B). The mobile phase was degassed by using an in-line Degassex Model DG4400 vacuum degasser (Phenomenex, Torrence, Calif.). The HPLC system was equilibrated at 10 k psi with 100% mobile phase A, and then a mobile phase selection valve was switched 20 min after injection, which created a near-exponential gradient as mobile phase B displaced A in a 2.5 mL active mixer. A 30-cm length of 360 µm o.d.×15 µm i.d. fused silica tubing was used to split ~20 µL/min of flow before it reached the injection valve (5 µL sample loop). The split flow controlled the gradient speed under conditions of constant pressure operation (10 k psi). Flow rate through the capillary HPLC column was ~900 nL/min. ThermoScientific LTQ linear ion trap mass spectrometer (ThermoScientific, San Jose, Calif.) was coupled with the LC-system using a in-house electrospray ionization (ESI) interface for all sample analysis. Home-made 150 µm o.d.×20 µm i.d. chemically-etched electrospray emitters were used (Anal Chem 2006, 78, (22), 7796-801). The heated capillary temperature and spray voltage were 200° C. and 2.2 kV, respectively. Data was acquired for 90 min, beginning 30 min after sample injection (10 min into gradient). Full spectra (AGC setting: $3\times10^4$) were collected from 400-2000 m/z followed by data-dependent ion trap MS/MS spectra (AGC setting: $1\times10^4$) of the ten most abundant ions applying collision energy of 35%. A dynamic exclusion time of 60 s was applied.

Peptide and Protein Identification Using MS/MS Spectra:

Peptides were identified from MS/MS spectra by matching them with predicted peptides from the protein FASTA file from the human International Protein Index (IPI—European Bioinformatics Institute) database (version 3.20, released at Aug. 22, 2006) containing 61,225 protein entries using the SEQUEST™ algorithm (J Am Soc Mass Spectrom 1994, 5, (11), 976-989). A standard parameter file allowing for a dynamic addition of oxidation to the methionine residue and a static (non-variable) carboxamidomethylation modification to the cysteine residue, with a mass error window of 3 Da units for precursor mass and 1 Da units for fragmentation mass was used. The searches were allowed for all possible peptide termini, i.e., not limited by tryptic-only termini. Peptide identifications were considered acceptable if they passed the thresholds determined acceptable for human plasma by Qian et al. (Mol Cell Proteomics 2005, 4, (5), 700-9) and passed an additional filter of a PeptideProphet score of at least 0.7 (Anal Chem 2002, 74, (20), 5383-92). The PeptideProphet score is representative of the quality of the SEQUEST™ identification and is based on a combination of XCorr, delCn, Sp, and a parameter that measures the probability that the identification occurred by random chance. PeptideProphet scores are normalized to a 0 to 1 scale, with 1 being the highest confidence value.

Protein Grouping:

Due to the high redundancy of peptide-to-protein relationships inherent in the IPI database, 2 protein grouping programs were used to consolidate sequence identifications. Protein Prophet (Anal Chem 2003, 75, (17), 4646-58) uses the identified peptide sequences to weight the probability that the peptide originated from a particular protein. When parent protein distinctions cannot be determined, those proteins are grouped together and assigned an index value.

Differentially Expressed Proteins:

Protein-level spectral counts were obtained by summing peptide-level spectral counts. To quantitatively compare relative protein abundances between different pools of samples, we considered either presence or absence of a particular protein in different phenotypes. For the proteins that were identified in multiple categories we used a cutoff criteria of fold change in log base(2) of spectral count with at least 5 spectral count in one of the phenotypes being compared.

ELISA Assays for Tamm-Horsfall Protein (UMOD):

A total of 60 urine samples (20 AR, 20 STA and 20 HC) were included. Urine samples diluted 200 fold in PBS buffer. The diluted 100 µL urine was incubated in Reacti-Bind 96-Well Plates over night at 4° C. The plate was washed 5 times with 1×PBS buffer containing 0.05% Tween 20. The wells were then blocked by 100 µL of 25% FCS in PBS to prevent non-specific binding of the antibody. The wells were then incubated with 1:3000 fold diluted anti-Tamm Horsfall Glycoprotein PAB at room temperature for hr. The color was developed by using turbo-TMB (Pierce Inc, Rockford, Ill.) and stopped by 100 µL 2M $H_2SO_4$ and the plate was read by SPECTRAMax 190 microplate reader (Molecular Devices, Sunnyvale, Calif.).

ELISA for Pigment Epithelium-Derived Factor—PEDF (SERPINF1), and CD44:

Sandwich ELISA assays were performed to validate the observed elevated level of PEDF and CD44 in urine collected from an independent set of patients and controls which included AR (n=20), STA (n=20), NS (n=8 for PEDF and 6 for CD44), HC (n=6).

PEDF ELISA:

An ELISA kit for Pigment Epithelium-Derived factor (PEDF) (BioProducts, MD) was used for the purpose and the reagents were prepared following the manufacturer's manual. Briefly, after an initial optimizing step for optimal dilution of urine, the urine samples were diluted (1:40) in Assay Diluent. The ELISA plate with 100 µL of standards and the diluted urine specimen was incubated at 37° C. for 1 h. After the incubation the plates were washed 5 times with Plate Wash Buffer. The wells were incubated with 100 µL PEDF detector antibody at 37° C. for 1 h and washed 5 times with the wash buffer. This step was followed by incubation of the wells with 100 uL Streptavidin Peroxidase Working solution.

CD44 ELISA:

An ELISA kit for CD44 (ABCam Inc, Cambridge, Mass.) was used for the purpose and the reagents were prepared following the manufacturer's manual. Briefly, after an initial optimizing step for optimal dilution of urine, the urine samples were diluted (1:1) in Standard Diluent Buffer. The ELISA plate with 100 µL of standards and the diluted urine was incubated at room temperature for 1 h. After the incubation the plates were washed 5 times with washing solution. The plate was incubated for 30 min with 50 µL of diluted biotinylated anti-CD44 in all wells. The plate was washed 5 times with the wash solution and was incubated with 100 µL HRP solution in all the wells for 30 min. This step was followed by a wash step. All the assays were developed by ready-to-use TMB substrate followed by addition of Stop Solution. All the plates were read by SPECTRAMax 190 microplate reader (Molecular Devices, Sunnyvale, Calif.). Protein concentrations were determined from a standard curve generated from the standards obtained with the kit.

Correlation Analysis Between the Spectral Counts and the Quantity Observed from ELISA Assay:

We obtained quantitative data for UMOD, pigment epithelial derived factor (PEDF), and CD44 using ELISA assays on an independent set of patients. The quantitative data obtained from ELISA was compared with the spectral count data for each protein observed in discovery phase using LC-MS/MS platform. P Values and Pearson correlation coefficients were calculated using SAS® program (SAS Corporate Statistics, Cary, N.C.).

Enrichment Analysis and Pathway Impact Analysis:

The enrichment analysis for identified proteins was performed using Ingenuity Pathway Analysis (http(colon)//www(dot)ingenuity(dot)com). A list of all human genes was used as reference for computing significance, which was obtained from the Onto-Tools database (Bioinformatics 2006, 22, (23), 2934-9). The pathway analysis was also performed using Pathway-Express (Bioinformatics 2009, 25, (1), 75-82 and Genome Res 2007, 17, (10), 1537-45). Pathway-Express performs a novel impact analysis on signaling pathways, which in addition to the number of proteins in IPA, considers important biological factors such as the topology of the pathway, position of the protein on the pathway, amount of change in protein expression, and the type of interaction between the protein in each pathway.

Results

Figure 3:
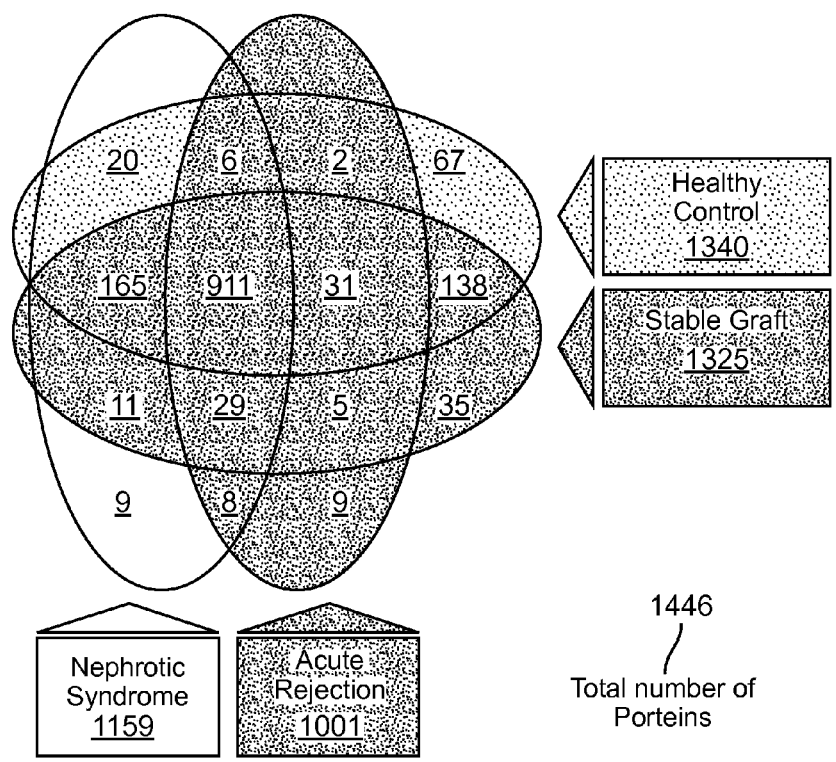
FIG. 3. Urinary proteins were identified from urine collected from healthy as well as renal patients with or without kidney transplant. Number of proteins identified in urine collected from renal transplant patients with biopsy proven acute rejection (AR), renal transplant patients with stable graft function (STA), healthy control (HC), and renal patients with nephrotic syndrome (NS).

Detection of Novel Urinary Proteins Expands the Urinary Proteome Database:

Using LC-MS/MS-based shotgun proteomics on urine from renal patients as well as healthy individuals, we identified 1446 urinary proteins. The criteria for a positive protein identification were a minimum of 2 unique, non-redundant peptides per protein to be identified, thus the FDR for protein identifications is ~0.1% based on decoy database searching while the FDR at unique peptide level is ~3.0%. We identified 1001, 1159, 1325, and 1340 proteins respectively in AR, NS, STA, and HC urine, respectively (FIG. 3). Using a database available through Ingenuity Pathway Analysis—IPA (Ingenuity® Systems, Redwood City, Calif.—www(dot)ingenuity(dot)com) on predicted proteins based on the human genome database (Nature 2001, 409, (6822), 860-921), we mapped the proteins identified with previously annotated urinary and proteins of renal origin. A total of 756 urinary proteins from our 1446 protein list have been listed as urinary proteins (UP) which leaves 690 proteins in our list of urinary proteins as novel urinary proteins labeled as novel urinary proteins (NUP). We compared the list of urinary proteins identified from healthy individuals in this study with 1543 identified by Adachi et al. (Genome Biol 2006, 7, (9), R80) and 1160 by Gonzales et al (J Am Soc Nephrol 2008). This study has added 560 new proteins in the existing urinary proteome of healthy urine.

Figure 4:
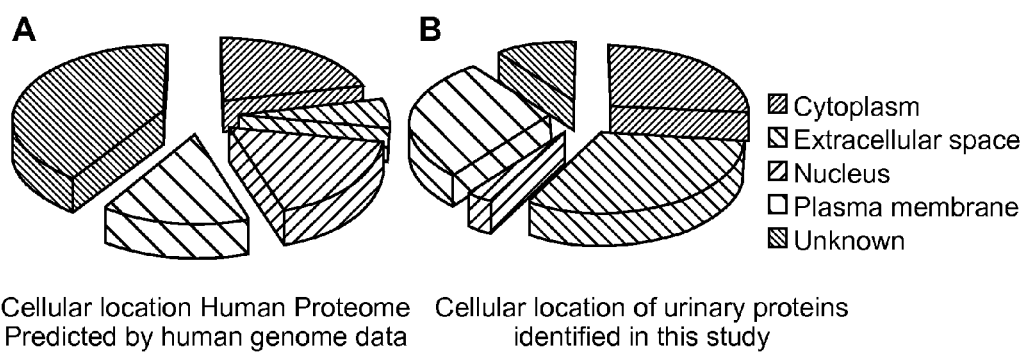
FIG. 4. A significant enrichment of extracellular and plasma membrane proteins was observed in urine. Pie chart presentation of distribution proteins in terms of cellular location (cytoplasmic, extracellular, nuclear and plasma membrane and unknown). (A) Distribution in human proteome based in human genome data. (B) The distribution proteins identified in this study.

Urinary Proteins are Enriched with Extracellular Proteins and Complement and Coagulation, Glycan Structures—Degradation, Cell Adhesion, and ECM-Receptor Interaction were Major Pathways:

Gene ontological classification (The Gene Ontology Consortium. Nat. Genet. 2000, 25, (1), 25-9) sub-grouped the 1446 identified proteins into 5 major groups; 279 were cytoplasmic proteins, 325 were extracellular proteins, 28 were nuclear proteins, 304 were plasma membrane, and 108 had as yet unknown sub-cellular localization. In agreement with previously reported results (Genome Biol 2006, 7, (9), R80), we found that extracellular and plasma membrane proteins were enriched and nuclear proteins were relatively underrepresented in the urine proteome when compared with the predicted human proteome from the human genome database (Nature 2001, 409, (6822), 860-921) (FIG. 4). Hypergeometric analysis reveals that the enrichment for proteins of extracellular origin (p<1.00E-6) and plasma membrane in urine (p<3.00E-6) is highly significant compared to human proteome. The major representing pathways were complement and coagulation cascades (P=1.95E-12), glycan structures—degradation (P=1.31E-11), cell adhesion molecules (CAMs) (P=1.77E-11), ECM-receptor interaction (P=1.87E-11), cell communication (P=2.04E-11), focal adhesion (P=2.62E-11), axon guidance (P=2.86E-11), regulation of actin cytoskeleton (P=4.97E-09), cytokine-cytokine receptor interaction (P=3.26E-09), hematopoietic cell lineage (P=4.89E-08).

No specific bias towards plasma and renal proteins in urine of renal patients and depletion of ECM-receptors and integrins in renal patients. We identified 1420 proteins detected in the urine of patients with normal renal function (HC and STA), while only 1206 proteins were found in patients with active renal dysfunction (AR and NS). There was no bias of the health status of the kidney in terms of known urinary, blood, and renal proteins when we used Ingenuity Pathway Analysis® based annotation. Among 1420 proteins identified in HC and STA combined 578, 463, and 434 proteins were previously known urinary, blood and renal proteins. Among 1206 proteins identified in AR and NS combined 504, 405, and 353 proteins were previously known urinary, blood, and renal proteins.

67 proteins were uniquely identified only in healthy urine (HC). EH-domain-containing protein 1 (EDH1) and creatinine kinase B-type (CKB) were the two most abundant proteins identified in this group. Among these proteins a significant number of proteins are known to be involved in cell morphology (CEACAM6, CR1, CRYAB, ERK, GNA12, GNA13, GNAQ, KDR, NOS3, PAFAH1B1, PP1CB, PTPRF, RAB4A, RYR2), metabolic disease and lipid metabolism (ACO1, CD7, DDC, EHD1, EXTL2, FAM125A, FLRT3, LPHN3, MAN2A2, PPIC, RAB4B, RABSB, SORD, VPS28, and VPS37D).

The spectral counts for the proteins measured by LC MS were compared and correlated to the concentration calculated from ELISA assays on an independent set of the urine samples from the similar phenotypes as used in the discovery phase. We observed a good correlation between the spectral counts and quantitative data measured from quantitative ELISA assays. When we combined total concentration measured from ELISA assay and compared to the spectral counts for corresponding samples, there was an excellent correlation ($R^2$=0.84) with P-value<0.0012 (Table 7).

TABLE 7

Quantitative measurement of THP, PEDF, and CD44: Protein concentration for these proteins were measured by ELISA and correlated the concentration obtained with the spectral count data observed from label-free LC MS.

| Protein Name | Samples | Concentration measured by ELISA assays (ng/µL) | | | | Spectral count |
|---|---|---|---|---|---|---|
| | | Minimum | Maximum | Median | Mean | |
| THP* | AR (n = 20) | 216.00 | 13000.00 | 4150 | 5504.50 | 126 |
| THP | STA (n = 20) | 374.00 | 56828.00 | 10248 | 13951.90 | 374 |
| THP | HC (n = 20) | 7424.00 | 66622.00 | 17865 | 19798.10 | 581 |
| PEDF** | AR (n = 20) | 10.00 | 1357.00 | 327 | 395.95 | 75 |
| PEDF | STA (n = 20) | 0.00 | 40.00 | 0 | 6.00 | 54 |
| PEDF | HC (n = 8) | 0.00 | 30.00 | 10 | 10.00 | 15 |
| PEDF | NS (n = 6) | 0.00 | 96.00 | 5 | 19.33 | 124 |
| CD44 | AR (n = 20) | 0.34 | 3.96 | 1.27 | 1.67 | 15 |
| CD44 | STA (n = 20) | 3.42 | 19.87 | 13.2 | 12.57 | 18 |
| CD44 | HC (n = 6) | 4.06 | 19.87 | 11.1 | 11.76 | 125 |
| CD44 | NS (n = 6) | 1.99 | 17.97 | 6.51 | 8.54 | 18 |
| Cumulative correlation among all the concentration and spectral counts for 3 proteins | | | | Correlation | 0.84 | |
| | | | | P value | <0.0012 | |

*THP: Tamm-Horsfall Protein (UMOD)
**PEDF: Pigment Epithelium Derived Factor (SERPINF1)

Differential Expression of Proteins in Acute Rejection (AR):

We analyzed relative abundance of proteins identified in both renal transplant patients with AR episode and those with stable graft (STA). There were 9 proteins that were identified only in AR urine but not in urine of HC, STA, and NS phenotypes including HLA class II histocompatibility antigen, DP(W4) beta chain (HLA-DBP), HLA class II histocompatibility antigen, DRB1-8 beta chain (IgHM), C4b-binding protein alpha chain (C4BPA), MHC class II antigen (HLA-DR), Myosin light chain 1 (MYL6B), HLA class II histocompatibility antigen DQ(3) beta chain (HLA-DQB1) (Table 4A) and a total of 68 proteins that were absent in AR but present in HC, STA, and NS categories that included Isoform 1 of Melanotransferrin (MFI2), Isoform 1 of FRAS1-related extracellular matrix protein 2 (FREM2), Isoform 2 of FRAS1-related extracellular matrix protein 2 (ROR1), Isoform 2 of Neural cell adhesion molecule L1-like protein (PLD3), Golgi apparatus protein 1 (CRYL1), and Thyrotropin-releasing hormone-degrading ectoenzyme (TRHDE).

Figure 5:
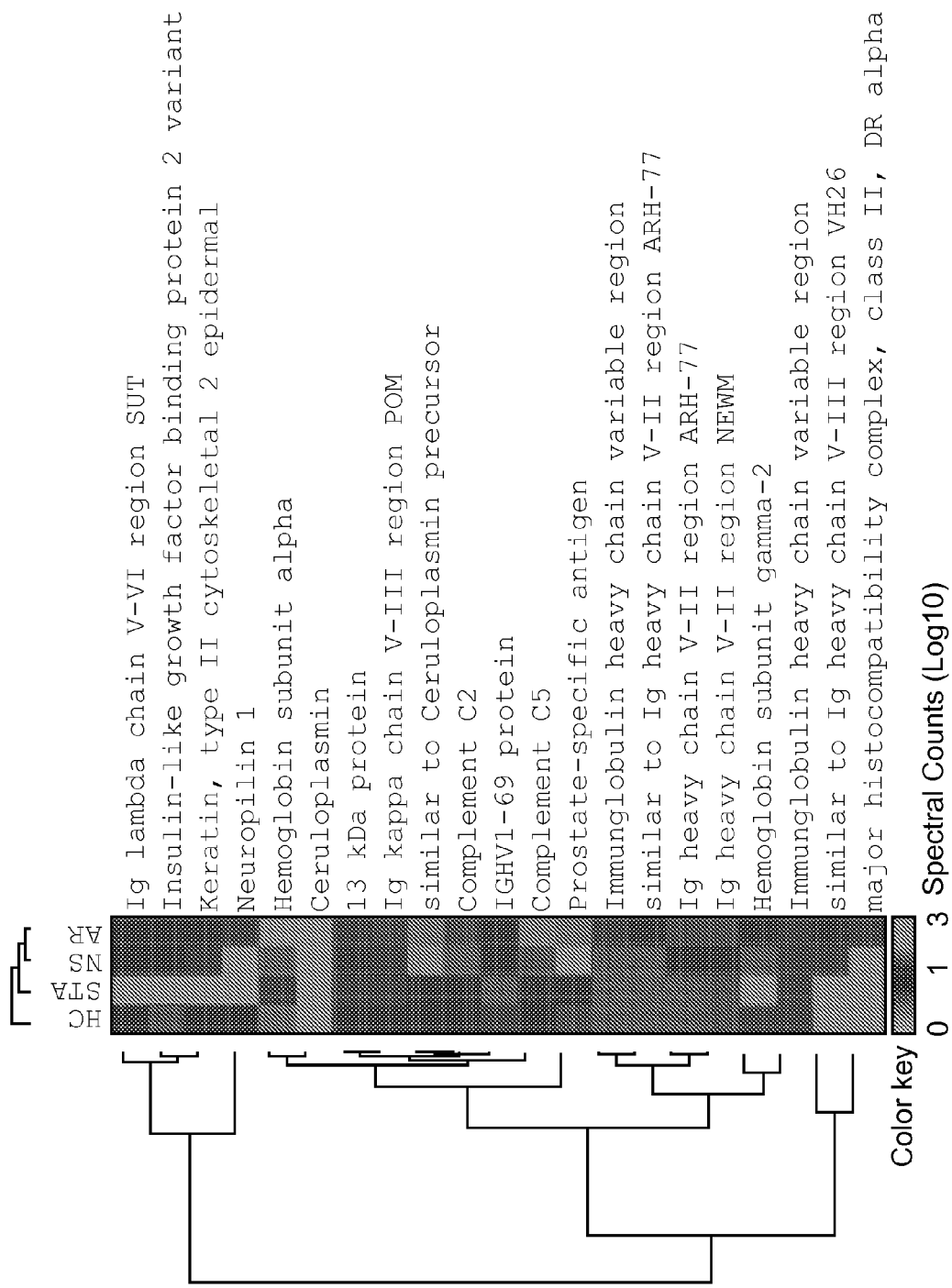
FIG. 5. A heat map demonstrating level of elevated proteins in AR compared to STA when compared to healthy urine and NS.

From their spectral counts evaluation all 9 collagens, COL5A3, COL4A2, COL1A2, COL27, COL1A1, COL15A1, COL6A1, COL12A1 identified were decreased in AR urine including type IV collagenase (MMP-9) and its inhibitor TIMP-1. A number of SERPIN family members SERPING, SERPINB12, SERPINB3, SERPINB4 were decreased in AR urine whereas two members SERPINC1 and SERPINF1 (PEDF) were increased. The down-regulated proteins were found to be involved in ECM-receptor interaction, cell communication, and Glycan structure degradation (all with P≤0.0005). We used up-regulated proteins in AR to generate a heat map (FIG. 5). The hierarchical clustering positioned NS next to AR in the heat map indicating there is a considerable injury involved in AR.

Verification of AR Associated Proteins Tamm-Horsfall Protein (UMOD), Pigment Epithelium-Derived Factor (PEDF), and CD44

Figure 6:
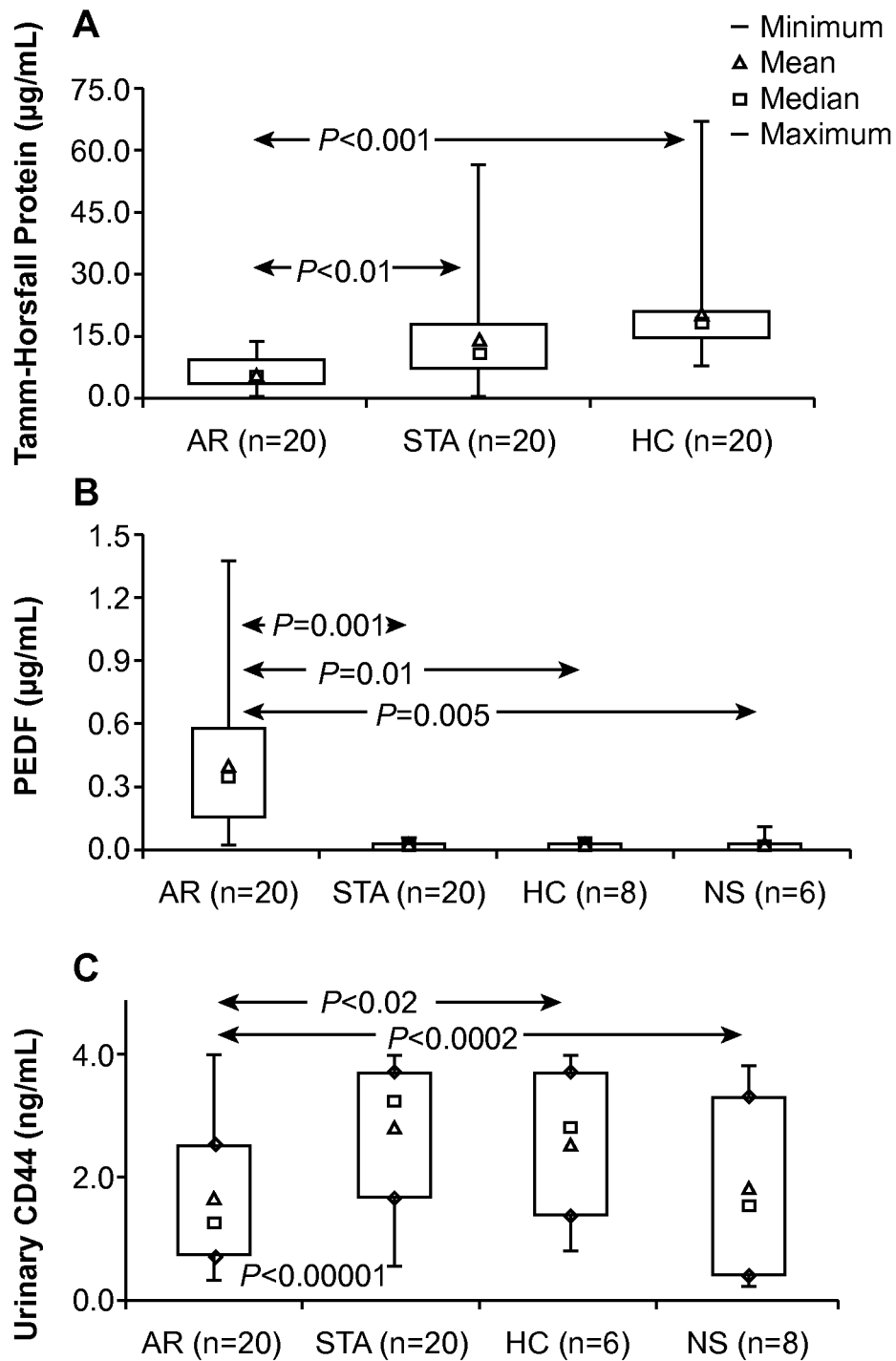
FIG. 6. Verification of discovery of potential biomarker candidates by ELISA assay. Urinary protein level of three candidate proteins, THP, PEDF, and CD44 were measured by ELISA using an independent set of samples from different phenotypes. (A) A decreased level of THP was observed in AR urine (n=20, mean concentration 5.50 µg/mL) when compared to STA urine (n=20, mean concentration 13.95 µg/mL) with P<0.01 and healthy control urine (n=20, mean concentration 19.80 µg/mL) with P<0.001. (B) An increased level of PEDF protein was observed in AR urine (n=20, mean concentration 0.40 µg/mL) when compared to STA urine (n=20, mean concentration 0.01 µg/mL) with P=0.0001, with healthy control urine (n=8, mean concentration 0.01 µg/mL) with P=0.02, and with nephrotic syndrome urine (n=6, mean concentration 0.02 µg/mL) with P=0.005. (C) A decreased level of CD44 protein was observed in AR urine (n=20, mean concentration 1.67 ng/mL) when compared to STA urine (n=20, mean concentration 12.57 ng/mL) with P<0.00001, with healthy control urine (n=6, mean concentration 11.76 ng/mL) with P<0.02, and with nephrotic syndrome urine (n=6, mean concentration 8.54 ng/mL) with P<0.0002. The boxes in the box plots are bounded by 75th and 25th percentiles of the data and the whiskers extend to the minimum and maximum values.

We performed ELISA assay on UMOD, PEDF, and CD44 as AR specific novel urinary proteins for verification. We verified the decreased UMOD in AR patients. ELISA assay was run for urinary UMOD was performed on an independent validation set of samples with AR (n=20), STA (n=20), and HC (n=20). The mean UMOD concentration in AR urine (5.50±0.85 µg/mL) was significantly lower than stable graft urine (13.95±2.94 µg/mL) (P<0.01) and healthy normal control urine (19.80±2.71 µg/mL) (P<0.001) (FIG. 6A). In another experiment on we observed elevated concentration of PEDF in AR urine compared to the urine collected from stable graft function and other controls that included healthy normal control and non-specific proteinuric patients. The mean PEDF concentration in AR urine (0.370±0.350 ng/mL) was significantly higher than STA urine (0.006±0.009 ng/mL) (P=0.0001), NS urine (0.019±0.037 ng/mL) (P=0.005), and HC urine (0.009±0.009 ng/mL) (P=0.005) (FIG. 6B). When we assayed CD44 in an independent sample set of individual urine samples we observed a decreased concentration of CD44 in AR urine compared to the urine collected from stable graft function and other controls that included healthy normal control and non-specific proteinuric patients. The mean CD44 concentration in AR urine (1.67±1.17 ng/mL) was significantly lower than STA urine (2.81±1.10 ng/mL) (P=0.0001), NS urine (1.83±1.63 ng/mL) (P=0.005), and HC urine (2.54±1.41 ng/mL) (P=0.005) (FIG. 6C).

Discussion

This study describes application of shotgun proteomics to expand the existing healthy normal urinary proteome database as well as its use in identification and verification of 3 potential biomarkers specific for AR of renal transplantation. As urine is the most relevant biofluid for biomarker discovery efforts for kidney diseases, its proteomic analysis is very relevant (Clin Transplant 2008, 22, (5), 617-623). Mass spectrometry-based proteomics provides a fast and accurate means of obtaining protein identification from complex samples and allows for rapid screening for disease markers (Mol Cell Proteomics 2006, 5, (10), 1727-44). Renal transplantation has remained the optimal treatment for patients with end-stage kidney disease (Pediatr Nephrol 2005, 20, (7), 849-53). Even though improvement in the short term survival of grafts has been reported, AR of renal transplant still remains the primary risk factor for graft functional decline, chronic rejection and graft loss. Therefore, identification of AR specific biomarkers is important for patient and allograft surveillance and treatment. Herein, we used LC-MS based proteomics to investigate urine from kidney transplant patients and have discovered protein biomarkers that provide a way to diagnose acute rejection effectively and non-invasively. For this discovery step, we used an initial pooling approach to minimize individual and disease heterogeneity, with subsequent verification of selected results in independent urine samples with similar clinical phenotypes that fed the discovery set pools.

Figure 7:
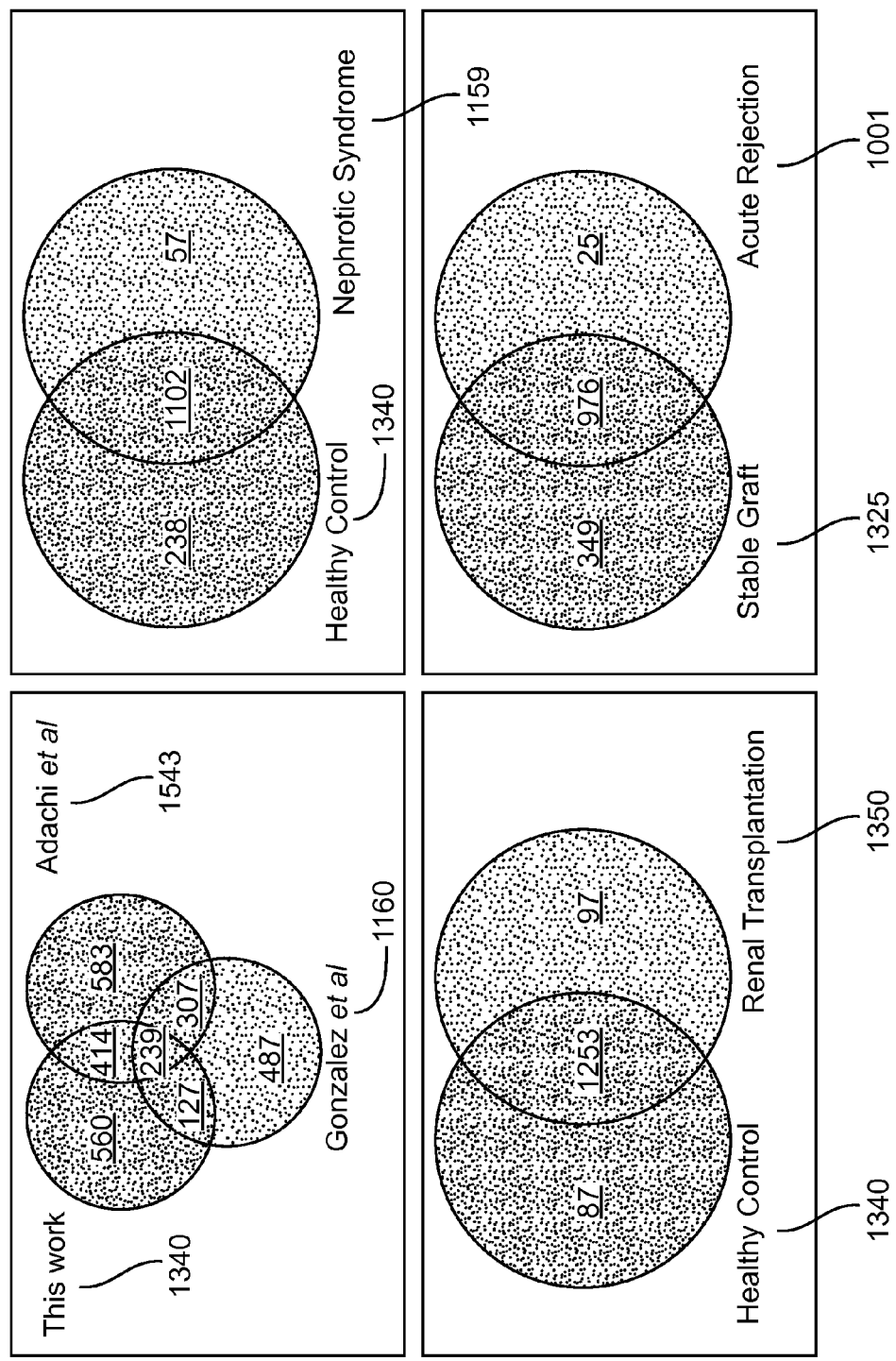
FIG. 7. Urinary proteins identified from different patients groups including the healthy controls (HC) were compared. [A] A Venn diagram to compare urinary proteins from healthy normal individuals identified in this study to the proteins identified by Adachi et al. (Genome Biol 2006, 7, (9), R80) and urinary proteins identified by Gonzalez, et al. (J Am Soc Nephrol 2008). [B] A comparison of proteins identified in healthy urine (HC) and urine of nephrotic syndrome (NS). [C] A comparison of proteins identified in healthy urine (HC) and urine of renal transplant patients both stable graft (STA) and acute rejection (AR) combined. [D] A comparison of proteins identified in urine from stable graft (STA) to urine of acute rejection (AR).

Different proteomic approaches have been applied to analyze urinary proteome in the past which has helped build up a list of urinary proteins identified to date (Mol Cell Proteomics 2006, 5, (3), 560-2; Proc Natl Acad Sci USA 2004, 101, (36), 13368-73; Proteomics 2005, 5, (18), 4994-5001; Proteomics 2004, 4, (4), 1159-74; Genome Biol 2006, 7, (9), R80; J Am Soc Nephrol 2008). Early studies used gel-based techniques to identify a relatively smaller number of proteins; whereas use of gel-free LC-MS has proven to be an efficient way to identify a greater number of proteins. Adachi et al identified 1543 proteins using urine collected from healthy individuals (Genome Biol 2006, 7, (9), R80). In a recent report, Gonzales et al have identified 1160 from human urinary exosomes (J Am Soc Nephrol 2008) (summarized in FIG. 7).

We have identified a new set of urinary proteins with stringent criteria of a minimum 2 unique, non-redundant peptides per protein with ~0.1% FDR for protein identification. As summarized in FIG. 7 there is a significant overlap among the list of proteins identified by Adachi et al (Genome Biol 2006, 7, (9), R80) and Gonzales et al (J Am Soc Nephrol 2008) yet there are new proteins identified in each study, which will eventually help to build a comprehensive human urinary proteome database. Apart from contributing to the existing urinary protein database, we have analyzed urinary proteins identified from healthy normal controls to nephrotic syndrome and renal transplantation which yielded specific proteins related to renal injury associated with nephrotic syndrome as well as renal transplantation that included AR and stable graft function.

One of the challenges of translational research is that there is a wide range (approximately as high as 10 orders of magnitude) of protein concentration present in the biospecimen, especially blood and urine. The experimental design applied in this study has provided us protein identifications for high abundant proteins such as UMOD with a concentration measured 5 orders of magnitude (~0.07 mg/mL) more than the concentration measured for protein S100 calcium binding A4 protein (~2 ng/mL) in urine. In this study we calculated spectral counts as a semi-quantitative means for comparison and a weighted fold-change was used to derive a list of potential biomarker proteins. We tested 3 proteins whose concentration differed by 4 orders magnitude, whereas there was a nearly perfect correlation to a good correlation of the proteins ranging from mean spectral counts 9 to 360 ($r2$=0.59-0.99). The data suggest that label free LC-MS/MS spectral count data provides relatively good quantitation for high abundance to moderate abundance proteins. If the spectral count is low, it has a poor correlation with the real concentration in the sample and may require more stringent labeling methods such as iTRAQ 35 or 18O/16O labeling method (36) to achieve more accurate quantitation. In this study, we used spectral counts as our measure of relative abundance to list potential AR specific proteins.

Given the scope of the study, we took three relevant protein candidates to verify their validity as being AR specific as discovered by the label-free approach using LC-MS/MS. Since ELISA assay is known to be robust, sensitive for performing quantitative measurements of proteins in a simple setting unlike MRM. We performed ELISA assay on THP, PEDF, and CD44 as AR specific novel urinary proteins. We have demonstrated that the reduced level of THP and CD44 and the elevated level of PEDF in AR urine could be verified as a highly specific and sensitive method to detect AR within the transplanted kidney, regardless of the confounding effect of proteinuria, immunosuppression, age or gender.

Tamm-Horsfall Protein (also known as uromodulin—UMOD) is localized in the epithelial cells of the thick ascending limbs of Henle's loop and the most proximal part of the distal convoluted tubule (37). This protein is suggested to be involved in constitutive inhibition of calcium crystallization (38). Mutation of the UMOD gene has been linked to familial juvenile hyperuricemic nephropathy (FJHN) as well as autosomal-dominant medullary cystic kidney disease (MCKD2) in children (J Med Genet. 2002, 39, (12), 882-92) and has also been reported to be involved in prevention of urinary tract infection (Eur J Clin Invest 2008, 38 Suppl 2, 29-38). This protein has intrigued nephrologists for long because of its high abundance in healthy urine with no obvious role (Nephron 2000, 85, (2), 97-102). Kaden et al observed reduced urinary UMOD delayed onset of transplanted function and increased urinary UMOD with recovery of kidney health (Urol Res 1994, 22, (3), 131-6). However, the use of UMOD as diagnostic parameter was not recommended. Sejdieu et al have recently related decreased UMOD in urine to development of renal failure and cardiovascular death within 20 years in type 1 but not in type 2 diabetes (Scand J Urol Nephrol 2008, 42, (2), 168-74). Our observation of reduced level of Tamm-Horsfall protein in AR does agree with the pattern of low urinary UMOD with poorly functioning graft and may need to be further validated with a larger cohort of patient samples.

Pigment epithelium-derived factor precursor (PEDF) is also known as serpin peptidase inhibitor. Clade F (SERPINF) is a member of serine protease inhibitors and is known to be a potent inhibitor of angiogenesis in the eye (Science 1999, 285, (5425), 245-8). PEDF was detected as one of the proteins whose level was elevated in the AR urine. PEDF is one of the major inhibitors of angiogenesis and is involved in physiological activities including wound healing, ischemia reperfusion injury and cancer metastasis to name a few. Even though no direct correlation has been established for PEDF in renal injury, in a recent report, Matsuyama et al observed an increased PEDF level in the serum of diabetic patients with both diabetic retinopathy and nephropathy and have suggested this could be a reflection of microvascular damage (Mol Vis 2008, 14, 992-6). Our observation of the increased level of PEDF in AR urine could provide a new way to monitor health status of renal transplant and a further investigation to understand underlying mechanism related to its involvement in AR.

CD44 is a cell-surface glycoprotein and is known to be involved in cell-cell interactions, cell adhesion and migration (Nat Rev Mol Cell Biol 2003, 4, (1), 33-45). It acts as a receptor for hyaluronic acid (HA), osteopontin, collagens, and matrix metalloproteinases (MMPs) (Mol Pathol 1999, 52, (4), 189-96). A wide range of activities for this protein have been reported which include lymphocyte activation, recirculation and homing, hematopoiesis, and tumor metastasis. Transcripts for this gene undergo complex alternative splicing that results in many functionally distinct isoforms, however, the full length nature of some of these variants has not been determined. In a separate study in our lab to investigate potential AR biomarkers using serum ELISA, CD44 has been observed to be up-regulated in AR serum (p=0.01) with 65% sensitivity and 70% specificity (Chen et al, manuscript submitted for publication). Our observation of decreased level of this protein in AR urine has the opposite trend to serum CD44 level and is interesting as one can hypothesize that there is alteration of glomerular filtration efficiency of this protein at the time of AR.

High throughput genomic or proteomics studies not only generate a list of disease specific genes or proteins but also help in understanding underlying molecular pathways and events. The biological activity and their association to different pathways provides a better understanding of the acute rejection event which is generally known to be mediated by T Cell responses to antigens from donor organs which are different than the ones in the recipient. This study has provided a broad view of underlying events in the kidney at the time of acute rejection. We observed upregulation of MHC proteins which are involved in the presentation of foreign antigens to T cells.

By impact analysis on signaling pathways, we identified a number or AR specific urinary proteins that are part of the acute phase response, complement and coagulation cascades. On the other hand, there is a significant down-regulation of proteins involved with ECM, cytoarchitecture in AR urine when compared to STA and healthy controls which suggested a significant turnover of extracellular matrix during AR episode.

CONCLUSION

In summary, in this first of its kind report, we have successfully demonstrated that shotgun proteomics is a viable way to discover potential biomarkers in transplantation. The outcome of this study demonstrates that comparative analysis strategy using pooled samples is a simple and effective way to achieve a list of potential biomarkers that can track with normal and disease states. Cross-validation of selected results from these studies, by an economically viable and convenient ELISA assay, in an independent set of urine samples, demonstrates the feasibility of the translation of this approach to clinical practice. In conclusion, this label-free, semi-quantitative approach to analyze the urinary proteome in normal and disease states provides a robust and sensitive method for detection of urinary proteins for serial, non-invasive clinical monitoring for graft rejection after kidney transplantation.

In addition to the Example above, see Sigdel et al., "Shotgun proteomics identifies proteins specific for acute renal transplant rejection" *Proteomics—Clinical Applications* Volume 4 Issue 1, Pages 32-47, incorporated by reference herein in its entirety (including all supplementary information retrievable via the internet, e.g., data and supplementary tables).

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

---

What is claimed is:

1. A method of evaluating the expression level of three or more genes in a sample from a subject who has received an organ allograft, wherein the three or more genes comprise GZMK, NKTR, and SLC25A37, wherein said evaluating comprises:
   contacting said sample with a collection of primers or probes for selectively amplifying an expression product of each of said three or more genes, wherein the primers or probes are labelled and the collection comprises primers or probes for selectively amplifying 3 to 100 different genes; and
   assessing, using the collection of primers or probes, an amount of each of said expression products in said sample.

2. The method of claim 1, wherein said organ allograft is a kidney allograft, a heart allograft, a liver allograft, or a lung allograft.

3. The method of claim 1, wherein said evaluating further comprises evaluating the expression level of one or more genes of ABTB, ANK1, B2M, CFLAR, CHST11, DUSP1, EPOR, GBP2, IFNGR1, ITGAX, LYST, MAP2K3, MAPK9, NAMPT, PCTP, PSEN1, RNF130, RYBP, RARA, RXRA, and TNFRSF1A.

4. The method of claim 1, wherein said evaluating further comprises evaluating the expression level of one or more genes of ADAMS, ADAM19, ADAMTS3, AIF1, AIM2, ARHGAP4, ARHGDIB, ARPC1B, ATF5, BASP1, BATF, BBC3, BIRC5, BTN3A2, C1orf38, CASP4, CCL13, CD2, CD3D, CD6, CD7, CD8A, CD14, CD44, CD48, CD53, CDC20, CORO1A, CXCL10, CXCL9, DDB2, DDX11, DDX23, F13A1, FCER1G, FOXM1, FZD2, GZMA, HCP5, HLA-A, HLA-DMA, HLA-DQB1, HLA-E, HLA-F, HLA-G, IFITM3, IKBKE, IL2RB, IL10RA, IL15RA, INPP5D, IRF1, IRF3, IRF4, IRF5, ISG20, ITGB2, ITGB7, KRT17, LCK, LEF1, LGALS9, MAN2B1, MAP3K11, MAP4K1, MARCKS, MCM5, MDK, MMP9, NELL2, NKG7, NNMT, NUP210, PLCB2, PLEK, PML, POLR2A, PRKD2, PSMB9, PSME1, PTPRC, PTPRCAP, RAB27A, RGS10, RUNX3, SERPINH1, SH2D2A, STAB1, STAT1, STK10, TAP1, TNF, TNFAIP2, TNFRSF1B, TNFRSF9, TNFRSF14, UCP2, VAMP5, and ZAP70.

5. The method of claim 1 wherein said three or more genes are differentially expressed in monocytes.

6. The method of claim 3, wherein said evaluating further comprises evaluating the expression level of DUSP1, PSEN1, ITGAX and CFLAR.

7. The method of claim 1, wherein the expression level of 5 or more genes is measured.

8. The method of claim 1, wherein the expression level of 10 or more genes is measured.

9. The method of claim 1, wherein said evaluating further comprises evaluating the expression level of CFLAR, DUSP1, EPOR, PSEN1, RARA, EPOR and RYBP.

10. The method of claim 1, wherein the expression level of 20 or more genes is measured.

11. The method of claim 1, wherein the sample is blood.

12. The method according to claim 1, wherein said assessing is quantitative.

13. A method of determining whether a subject who has received an organ allograft has a graft tolerant or a graft intolerant phenotype comprising:

(a) obtaining a peripheral blood sample comprising a peripheral blood monocyte from a subject;

(b) evaluating the level of expression of at least one gene in said peripheral blood sample to obtain a gene expression result, wherein said at least one gene is selected from the group consisting of: GZMK, NKTR, and SLC25A37, and wherein said evaluating comprises:

extracting mRNA from said sample; contacting said mRNA with a reagent for assaying said mRNA from said at least one gene;

assessing, using said reagent, the amount of said mRNA from said at least one gene in said sample;

(c) comparing said gene expression result to at least one reference gene expression profile, wherein said reference gene expression profile is selected from: an acute rejection phenotype gene expression profile and a control phenotype gene expression profile; and (d) determining that said subject is undergoing an AR response based on said comparing when said gene expression result of said three or more genes is similar to said acute rejection phenotype gene expression profile and/or is dissimilar to said control phenotype gene expression profile; or determining that said subject is not undergoing an AR response based on said comparing when said gene expression result is dissimilar to said acute rejection phenotype gene expression profile and/or is similar to said control phenotype gene expression profile.

14. A method of treating a transplant recipient, said method comprising:

(a) evaluating whether said transplant recipient has an acute rejection phenotype or a non-acute-rejection phenotype by using a gene expression result that was previously obtained from a quantitative determination of the nucleic acid expression levels of three or more genes comprising GZMK, NKTR, and SLC25A37;

(b) comparing said previously obtained gene expression result to at least one reference gene expression profile, wherein said reference gene expression profile is selected from: an acute rejection phenotype gene expression profile and a control phenotype gene expression profile;

(c) determining that said transplant recipient has an acute rejection phenotype based on said comparing when said gene expression result is similar to said acute rejection phenotype gene expression profile and/or is dissimilar to said control phenotype gene expression profile; and determining that said transplant recipient has a non-acute-rejection phenotype based on said comparing when said gene expression result is dissimilar to said acute rejection gene expression profile and/or is similar to said control phenotype gene expression profile; and (d) treating said transplant recipient by increasing immunosuppressive therapy if said transplant recipient is determined to have an acute rejection phenotype and decreasing immunosuppressive therapy if said transplant receipt is determined to have a non-acute-rejection phenotype.

15. The method of claim 13, wherein the method has a p value that is less than 0.05.

16. The method of claim 13, wherein the method has a specificity that is higher than 80%.

17. The method of claim 13, wherein the method has a sensitivity that is higher than 80%.

18. The method of claim 13, wherein the method has a ROC that is higher than 70%.

19. The method of claim 13, wherein the method has an AUC that is higher than 70%.

20. The method of claim 13, wherein the method has a positive predictive value that is higher than 70%.

21. The method of claim 13, wherein the method has a negative predictive value that is higher than 70%.

22. The method according to claim 13, wherein said reference gene expression profile is from a subject having a stable graft.

23. The method according to claim 13, wherein said comparing step comprises at least one of: comparing digital images of the expression profiles and comparing databases of expression data.

* * * * *